(12) United States Patent
Smith

(10) Patent No.: US 7,049,120 B2
(45) Date of Patent: May 23, 2006

(54) REGULATION OF HUMAN MRP5-LIKE PROTEIN

(75) Inventor: Timothy J. Smith, Cambridge, MA (US)

(73) Assignee: Bayer HealthCare AG, Leverkusen (DE)

(*) Notice: Subject to any disclaimer, the term of this patent is extended or adjusted under 35 U.S.C. 154(b) by 193 days.

(21) Appl. No.: 10/468,842

(22) PCT Filed: Mar. 8, 2002

(86) PCT No.: PCT/EP02/02554

§ 371 (c)(1),
(2), (4) Date: Sep. 3, 2003

(87) PCT Pub. No.: WO02/072825

PCT Pub. Date: Sep. 19, 2002

(65) Prior Publication Data

US 2004/0077833 A1    Apr. 22, 2004

Related U.S. Application Data

(60) Provisional application No. 60/323,334, filed on Sep. 20, 2001, provisional application No. 60/274,233, filed on Mar. 9, 2001.

(51) Int. Cl.
*C12N 9/14* (2006.01)
*C12N 15/00* (2006.01)
*C12N 1/20* (2006.01)
*C07H 21/04* (2006.01)
*C07K 1/00* (2006.01)

(52) U.S. Cl. .............. 435/195; 435/252.2; 435/320.1; 435/325; 530/350; 424/94.6; 536/23.2

(58) Field of Classification Search ............... 435/195, 435/320.1, 252.3, 6, 18; 530/350; 424/94.6; 536/23.2
See application file for complete search history.

(56) References Cited

U.S. PATENT DOCUMENTS 6,162,616 A    12/2000    Shyjan
2003/0059793 A1*    3/2003    Rosier et al. ............ 435/6

FOREIGN PATENT DOCUMENTS

WO    WO/01 32706    5/2001
WO    0132706    *    5/2005

OTHER PUBLICATIONS

Database EMBL "Online" Sep. 15, 1999, Poustka et al: *Homo sapiens* mRNA; cDNA DKFZp434p2035, Database accession No. AL117406, XP002229865.
Belinsky M G et al: "Characterization of Moat-C and Moat-D New Members of the MRP/CMOAT Subfamily of Transporter Proteins" Journal of the National Cancer Institute. vol. 90, No. 22, Nov. 18, 1998, pp. 1735-1741, XP002921303, ISSN:0027-8874.
Klein Izabella et al: "An Inventory of the Human ABC proteins." Biochimica et Biophysica Acta, vol. 1461, no 2, Dec. 6, 1999, pp. 237-262, XP004273095, ISSN: 0006-3002.
Borst Piet et al: "The multidrug resistance protein family." Biochimica et Biophysica Acta, vol. 1461, No. 2, Dec. 6, 1999, pp. 347-357, XP004273102, ISSN: 0006-3002.
Wijnholds Jan et al: "Multidrug-resistance protein 5 is a multispecific organic anion transporter able to transport nucleotide analogs." Proceedings of the National Academy of Sciences of the United States, vol. 97, No. 13, Jun. 30, 2000, pp. 7476-7481, XP002229864, ISSN: 0027-8424.
ABC transporters in lipid transport, Borst P, Zelcer N, van Helvoort A, Biochim Biophys Acta Jun. 26, 2000;1486(1).
ABC1: the gene for Tangier disease and beyond, Ordovas JM, Nutr Rev Mar. 2000;58(3 Pt 1):76-9.
Multidrug resistance, Schneider E, Paul D, Ivy P, Cowan KH, Cancer Chemother Biol Response Modif 1999;18:152-77.
The multidrug resistance protein 5 functions as an ATP-dependent export pump for cyclic nucleotides,Jedlitschky G, Burchell B, Keppler D, J Biol Chem. Sep. 29, 2000;275(39):30069-74.
Multidrug-resistance protein 5 is a multispecific organic anion transporter able to transport nucleotide analogs, Wijnholds J, Mol CA, van Deemter L, de Haas M, Scheffer GL, Baas F, Beijnen JH, Scheper RJ, Hatse S, De Clercq E, Balzarini J, Borst P, Proc Natl Acad Sci U S A. Jun. 20, 2000;97(13):7476-81.

* cited by examiner

*Primary Examiner*—Maryam Monshipouri
(74) *Attorney, Agent, or Firm*—Banner & Witcoff, Ltd.

(57) ABSTRACT

Reagents that regulate human MRP5-like protein and reagents which bind to human MRP5-like protein gene products can play a role in preventing, ameliorating, or correcting dysfunctions or diseases including, but not limited to, cardiovascular disorders, cancer, and CNS disorders.

16 Claims, 32 Drawing Sheets

Fig. 1 atgactagga agaggacata ctgggtgccc aactcttctg gtggcctcgt gaatcgtggc
atcgacatag gcgatgacat ggtttcagga cttatttatc ccctgacaa tgctggcctg
ttctcctacc tcacgtgtc atggctcacc ccgctcatga tccaaagctt acggagtcgc
         ttagatgaga acaccatccc tccactgtca gtccatgatg cctcagacaa aaatgtccaa
         aggcttcacc gcctttggga agaagaagtc tcaaggcgag ggattgaaaa agcttcagtg
         cttctggtga tgctgaggtt ccagagaaca aggttgattt tcgatgcact tctggcatc
         tgcttctgca ttgccagtgt actcgggcca atattgatta taccaaagat cctggaatat
         tcagagagc agttggggaa tgttgtccat ggagtgggac tctgctttgc ccttttctc
         tccgaatgtg tgaagtctct gagtttctcc tccagttgga tcatcaacca acgcacagcc
         atcaggttcc gagcagctgt ttcctccttt gcctttgaga agctcatcca attaagtct
         gtaatacaca tcacctcagg agaggccatc agctcttca ccggtgatgt aaactacctg
         tttgaagggg tgtgctatgg accctagta ctgatcacct gcgcatcgct ggtcatctgc
         agcattcct cctacttcat tattggatac actgcattta ttgccatctt atgctatctc
         ctggttttcc cactggcggt attcatgaca agaatggctg tgaaggctca gcatcacaca
         tctgaggtca gcgaccagcg catccgtgtg accagtgaag ttcctcacttg cattaagctg
         attaaaatgt acacatggga gaaaccattt gcaaaaaatca ttgaagacct aagaaggaag
         gaaaggaaac tattggagaa gtgcgggctt gtccagagcc tgacaagtat aaccttgttc
atcatcccca cagtggccac agcggtctgg gttctcatcc acacatcctt aaagctgaaa
ctcacgcgt caatggcctt cagcatggcct gcctccttga atctccttcg gctgtcagtg
ttctttgtgc ctattgcagt caaaggtcag acgaattcca agtctgcagt gatgaggttc
aagaagtttt tcctccagga gagccctgtt ttctatgtcc agacattaca agacccage

Fig. 1 (continued)

```
aaagctctgg tctttgagga ggccaccttg tcatggcaac agacctgtcc cgggatcgtc
aatggggcac tggagctgga gaggaacggg catgcttctg aggggatgac caggcctaga
gatgccctcg ggccagagga agaagggaac agcctgggcc cagagttgca caagatcaac
ctggtgtgg ctatgctgtc ccaacacttg tatgtcctcc ttggcttgca ggggatgatg
ttagggtct gcggcaacac ggggagtggt aagagcagcc tgttgtcagc catcctggag
gagatgcact tgctcgaggg ctcggtgggg gtgcagggaa gcctggccta tgtcccccag
caggcctgga tcgtcagcgg gaacatcagg gagaacatcc tcatgggagg cgcatatgac
aaggcccgat acctccagt gctccactgc tgctccctga atcgggacct ggaacttctg
ccctttggag acatgacaga gattggagag cgggcctca acctctctgg ggggcagaaa
cagaggatca gcctggcccg cgcgtctat tccgaccgtc agatctacct gctggacgac
ccctgtctg ctgtggacgc ccacgtcggg aagcacattt ttgaggagtg cattaagaag
acactcaggg ggaagacggt cgtcctggtg accaccagc tgcagtactt agaattttgt
ggccagatca ttttgttgga aaatgggaaa atctgtgaaa atggaactca cagtgagtta
atgcagaaaa agggaaata tgcccaactt atccagaaga tggaactcg agccacttcg
gtgagtcctg ccccactgcc ctcactaccc acgtggacg cacgtgtact cagggcctgt
gctctctccc caggacatgt tgcaggacac agcaaagata gcagagaagc caaagtgccg
gagcatcagc tcacacagga ggaggagatg gaagaaggct ccttgagttg gagggtctac
caccactaca tccagcagc tggaggttac atggtctctt gcataatttt cttcttcgtg
gtgctgatcg tcttcttaac gatcttcagc ttctggtggc tgagctactg gttggagcag
ggctcggggg tgagtgccat gagccgagag agcaatggaa ccatggcaga cctgggcaac
attgcagaca atcctcaact gtccttctac cagctggtgt acgggctcaa cgccctgctc
ctcatctgtg tggggtctg ctcctcaggg attttcacca aagtcacgag gaaggcatcc
acggccctgc acaacaagt gtttccgct gccccatgag tttctttgac
accatcccaa taggccggct ttgaactgc ttcgcagggg acttggaaca gctggaccag
ctccttgccca tctttcaga gcagttcctg gtcctgtcct taatggtgat cgccgtcctg
```

Fig. 1 (continued)

```
ttgattgtca gtgtgctgtc tccatatatc ctgttaatgg gagccataat catgttatt
tgcttcattt attatatgat gttcaagaag gccatcggtg tgttcaagag actgagaac
tatagccggt ctcctttatt ctccacatc ctcaattctc tgcaaggcct gagctccatc
catgtctatg gaaaaactga agacttcatc agccagttta agaggctgac tgatgcgcag
aataactacc tgctgttgtt tctatcttcc acacgatgga tggcattgag gctggagatc
atgaccaacc ttgtgacctt ggctgttgcc ctgttcgtgg cttttggcat ttcctccacc
ccctactcct ttaaagtcat ggctgtcaac atcgtgctgc agctggcgtc cagcttccag
gccactgccc ggattggctt ggagacagag gcacagttca cggctgtaga gaggatactg
cagtacatga agatgtgtgt ctcggaagct cctttacaca tggaaggcac aagttgtccc
caggggtggc cacagcatgg ggaaatcata tttcaggatt atcacatgaa atacagagac
aacacaccca ccgtgcttca cggcatcaac ctgaccatcc gcggccacga agtggtgggc
atcgtgggaa ggacgggctc tgggaagtcc tccttgggca tggctctctt ccgcctggtg
gagcccatgg caggccggat tctcattgac ggcgtggaca tttgcagcat cggcctggag
gacttgcggt ccaagctctc agtgatccct caagatccag tgctgctctc aggaaccatc
agattcaacc tagatcccct tgaccgtcac actgaccagc agatctggga tgccttggag
aggacattcc tgaccaaggc catctccaaag ttcccaaaa agctgcatac agatgtggtg
gaaaacggtg gaaacttctc tgtgggggag aggcagctgc tctgcattgc caggctgtg
cttcgcaact ccagatcat ccttatcgat gaagccacag cctccattga catggagaca
gacaccctga tccagcgcac aatccgtgaa gccttccagg gctgcaccgt gctgtcatt
gcccaccgtg tcaccactgt gctgaactgt gaccacatcc tggttatggg caatgggaag
gtggtagaat ttgatcggcc ggagtactg cggaagaagc ctgggtcatt gttcgcagcc
ctcatggcca cagcc
```

Fig. 2

```
MTRKRTYWVP NSSGGLVNRG IDIGDDMVSG LIYPLDNAGL FSYLTVSWLT PLMIQSLRSR
LDENTIPPLS VHDASDKNVQ RLHRLWEEEV SRRGIEKASV LLVMLRFQRT RLIFDALLGI
CFCIASVLGP ILIIPKILEY SEEQLGNVVH GVGLCFALFL SECVKSLSFS SSWIINQRTA
IRFRAAVSSF AFEKLIQFKS VIHITSGEAI SFFTGDVNYL FEGVCYGPLV LITCASLVIC
SISSYFIIGY TAFIAILCYL LVFPLAVFMT RMAVKAQHHT SEVSDQRIRV TSEVLTCIKL
IKMYTWEKPF AKIIEDLRRK ERKLLEKCGL VQSLTSITLF IIPTVATAVW VLIHTSLKLK
LTASMAFSML ASLNLLRLSV FFVPIAVKGL TNSKSAVMRF KKFFLQESPV FYVQTLQDPS
KALVFEEATL SWQQTCPGIV NGALELERNG HASEGMTRPR DALGPEEEGN SLGPELHKIN
LVVAMLSQHL YVLLGLQGMM LGVCGNTGSG KSSLLSAILE EMHLLEGSVG VQGSLAYVPQ
QAWIVSGNIR ENILMGGAYD KARYLQVLHC CSLNRDLELL PFGDMTEIGE RGLNLSGGQK
QRISLARAVY SDRQIYLLDD PLSAVDAHVG KHIFEECIKK TLRGKTVVLV THQLQYLEFC
GQIILLENGK ICENGTHSEL MQKKGKYAQL IQKMHKEATS VSPAPLPSLP TVDARVLRAC
ALSPGHVAGH SKDSREAKVP EHQLTQEEEM EEGSLSWRVY HHYIQAAGGY MVSCIFFFV
VLIVFLTIFS FWWLSYWLEQ GSGVSAMSRE SNGTMADLGN IADNPQLSFY QLVYGLNALL
LICVGVCSSG IFTKVTRKAS TALHNKLFNK VFRCPMSFFD TIPIGRLLNC FAGDLEQLDQ
LLPIFSEQFL VLSLMVIAVL LIVSVLSPYI LLMGAIMVI SQFKRLTDAQ CFIYYMFKK AIGVFKRLEN
YSRSPLFSHI LNSLQGLSSI HVYGKTEDFI SQFKRLTDAQ NNYLLLFLSS TRWMALRLEI
MTNLVTLAVA LFVAFGISST PYSFKVMAVN IVLQLASSFQ ATARIGLETE AQFTAVERIL
QYMKMCVSEA PLHMEGTSCP QGWPQHGEII FQDYHMKYRD NTPTVLHGIN LTIRGHEVVG
IVGRTGSGKS SLGMALFRIV EPMAGRILID GVDICSIGLE DLRSKLSVIP QDPVLLSGTI
RFNLDPFDRH TDQQIWDALE RTFLTKAISK FPKKLHTDVV ENGGNFSVGE RQLLCIARAV
LRNSKIILID EATASIDMET DTLIQRTIRE AFQGCTVLVI AHRVTTVLNC DHILVMGNGK
VVEFDRPEVL RKKPGSLFAA LMATA
```

Fig. 3

MKDIDMGKEY IIPSPGYRSV RDRSTIPGQH GDREEPRFRR TRSLECQDAL ETAARVEGLS
LDISVHSHLQ ILDEEHTKGK YHHGLSALKP FRTTTKHQHP VDNAGLFSYM TFSWLSPLAQ
VVHKKGELLM EDVWPLSKYE SSDVNCRRLE RLWQEELNEV GPDAASLRRV VWIFCRTRLI
LSIVCLMITQ LAGFSGPAFV VKHLLEYTQA TESNLQYSLL LVLGLLITEV VRSWSLALTW
ALNYRTGVRL RGAVLTMAFK KILKLKNIKE KSLGELINIC SNDGQRMFEA AAVGSLLAGG
PVVAILGMIY NVIILGPTGF LGSAVFILFY PAMMFVSRLT AYFRRKCVAA TDDRVQKMNE
VLTYIKFIKM YAWVKAFSQC VQKIREEERR ILEKAGYFQS ITVGVAPIVV VIASVVTFSV
HMTLGFDLTA AQAFTVVTVF NSMTFALKVT PFSVKSLSEA SVAVDRFKSL FLMEEVHMIK
NKPASPHIKI EMKNATLAWD SSHSSTQSSP KLTPKVKKDK RAPKGKKEKS RQLQHTEHQA
VLAEQKGHLL LDSDERPSPE EEEGKQIHAG SMRLQRTLYN IDLEIEEGKL VGICGSVGSG
KTSLISAILG QMTLLEGSIA VSGTFAYVAQ QAWILNATLR DNILFGKEFD EERYNSVLNS
CCLRPDLAIL PNSDLTEIGE RGANLSGGQR QRISLARALY SDRSIYILDD PLSALDAHVG
NHIFNSAIRK RLKSKTVLFV THQLQYLVDC DEVIFMKEGC ITERGTHEEL MNLNGDYATI
FNNLLGETP PVEINSKKEA SGSQKSQDKG PKPGSVKKEK AVKSEEGQLV QVEEKGQGSV
PWSVYWVYIQ AAGGPLAFLV IMVLFMLNVG STAFSTWWLS YWIKQGSGNS TVFEGNRSSV
SDSMRDNPFL QYYASIYALS MAVMLILKAI RGVVFVKGTL RASSRLHDEL FRRILRSPMK
FFDTTPTGRI LNRFSKDMDE VDVRLPFQAE MFIQNVILVF FCVGMIAGVF PWFLVAVGPL
LILFSVLHIV SRVLIRELKR LDNITQSPFL SHITSSIQGL ATIHAYNKRQ EFLHRYQELL
DDNQAPFFLF TCAMRWLAVR LDLISIALIT TTGLMIVLMH GQIPSAYAGL AISYAVQLTG
LFQFTVRLAS ETEARFTSVE RINHYIKTLS LEAPARIKNK APPHDWPQEG EITFENAEMR
YRENLPLVLK KVSFTIKPKE KIGIVGRTGS GKSSLGMALF RLVELSGGCI KIDGVRISDI
GLADLRSKLT IIPQEPVLFS GTVRSNLDPF NQYTEEQIWD ALERTHMKEC IAQLPLKLES
EVMENGDNFS VGERQLLCIA RALLRHCKIL ILDEATAAMD TETDLLIQET IREAFADCTM
LTIAHRLHTV LGSDRIMVLA QGQVVEFDTP SVLLSNDSSR FYAMCAAAEN KVAVKG

Fig. 4

GGTGGATCATCAACCAACGCGACAGCCATCAGGTTCCGAGCAGCTGTTCCTCCTTTGCC
TTTGAGAAGCTCATCATCCAATTTAAGTCTGTAATACACATCACCTCAGGAGAGGCCATCAGC
TTCTTCACCGGTGATGTAAACTACCTGTTTGAAGGGGTGCTATGGACCCCTAGTACTG
ATCACCTGCGCATCGCTGGTCATCTGCAGCCATTTCTTCCTACTTCATTATTGGATACACT
GCATTTATTGCCATCTTATGCTATCTCCTGGTTTTCCCATTGGCGGTATTCATGACAAGA
ATGGCTGTGAAGGCTCGGCATCACACATCTGAGGTCAGGACCAGCGCATCCGTGTGACC
AGTGAAGTTCTCACTTGCATTAAGCTGATTAAAAATGTA

Fig. 5

TGTGGTCTGGACTCGCTGGTGGCTGGTAGGGCACATTAAAGTCCCTTTTACCTAGGAGAG
CCCCAAGGTCCTGGAGGGCAGTGGGCCCTGGGCACTGCCTGCTGTGCCTGAGCCAGGC
TCTGTCCCTTGGCCCAATTGGTCCTGAGGCTGACTCATTCTGCCGCAGATGCACTTGCT
CGAGGGCTCGGTGGGGTGCAGGGAAGCCTGGCCTATGTCCCCAGCAGGCCTGGATCGT
CAGCGGGAACATCAGGAGAACATCCTCATGGGAGGCGCATATGACAAGG

Fig. 6

ATGACAGCCCAGGATGGTGCTTTGCAGCCGATGTGCCCTTCAGAAGGCGGCTCCGCACCAG
CTGCAGGTTGCGGGCCGAGTCCACGCTGGTGCGCTGGTGGAGCCGGCAGCAGGACGCC
CTCGTGGGTGAGCAGCACGCGGGAGGCGACTGGGATCTGATGGGGCTCACTGATGACA
TGCTGGCAGCCTTTCGCACTGGGGGCTGTCAAAAAGAGCCAGACAGCAGCTGCCCCGG
CCTGCCCCGCAGTCACCAAACCTCAGAACCCGCCCTCCACGCCTTCCGCTTCCGCGC
TACGGTCCGTCCCCGGCCCAAAAGCCATGGCTTCGCGCTGCTCTAGGAGAGCCTCCC
GAATTGGCAGGAACTGAAAATGACTAGGAAGAGGACATACTGGTGCCCAACTCTTCTGG
TGGCCTCGTGAATCGTGGCATGACATAGGCGATGACATGGTTTCAGGACTTATTATAA
AACCTATACTCTCCAAAGAATGGCCCCTGGAGTCAGCAAGAGAGACATCCTGAGGCTCCAG
GGAGGGCAGCTGTCCCACCGTGGCGAAGTAATGATGCCTGCCTTGAGAACCATGATTCC
CTTTCCGTCTCCCAAGCCGGAGGTTTCCTGCACCCAGGCCTGGACAAGTGGTTGGCATGT
TCTTCGTAACCTCACCGTGTCACCTGTCATGGTCACCCTCCACTGTCAGGCAGGATTGGCCTCCA
GTTAGATGGANGCAACCATCCCCTCTTTGAGAAAAAAGACGCTAAGGCGGGCTGACACAGCCCAGCCGC
GTCAGCGGTTACACGGCTTCAGGCAGGATTGGCCTCGGACCAGAATT
CACGGGTGAGCAGCAGATACACAGTGTGGGTCTCGAAGCGGAGGCAGGACGTG

Fig. 7

BLASTP - alignment of LBRI_312_protein against
swissnew|Q9QYM0|MRP5_RAT
MULTIDRUG RESISTANCE-ASSOCIATED PROTEIN
5.//:trembl|AB020209|AB020209_1 gene: "MRP5"; product: "multidrug resistance
protein (MRP5)"; Rattus norvegicus mRNA for multidrug resistance protein(MRP5)
complete cds.

```
  This hit is scoring at : 0.0 (expectation value)
  Alignment length (overlap) : 1343
  Identities : 40 %
  Scoring matrix : BLOSUM62 (used to infer consensus pattern)
  Database searched : nrdb_1_;
```

Q: 33 YPLDNAGLFSYLTVSWLTPL-MIQSLRSRLDENTIPPLSVHDASDKNVQRLHRLWEEEVS
      :P:DNAGLFSY:T.SWL:PL :  .  :.L  .: PLS :::SD N.:RL.RLW:EE::
H: 99 HPVDNAGLFSYMTFSWLSPLAQVVHKKGELLMEDVWPLSKYESSDVNCRRLERLWQEELN

RRGIEKASVLLVMLRFQRTRLIFDALLGICFCIASVLGPILIIPKILEYSEEQLGNVVHG
   . G :.AS: V: F RTRLI..:.  :  :A.. GP..:...:LEY:... N: ..
   EVGPDAASLRRVVWIFCRTRLILSIVCLMITQLAGFSGPAFVVKHLLEYTQATESNLQYS

Fig. 7 (continued)

```
VGLCFALFLSECVKSLSFSSSWIINQRTAIRFRAAVSSFAFEKLIQFKSVIHITSGEAIS
: L..L.L:E.V:S S.: :W.:N.RT.:R.R.AV :AF:K:::.K:: . GE.I:
LLLVLGLLLTEVVRSWSLALTWALNYRTGVRLRGAVLTMAFKKILKLNIKEKSLGELIN

FFTGDVNYLFEGVCYGPLVLIITCASLVICSISSYFIIGYTAFIAILCYLLVFPLAVFMTR
. :D . :FE....G.L. . .: I ...I:G T.F: . :::L..P..:F::R
ICSNDGQRMFEAAAVGSLLAGGPVVAILGMIYNVIILGPTGFLGSAVFILFYPAMMFVSR

MAVKAQHTSEVSDQRIRVTSEVLTCIKLIKMYTWEKPFAKIIEDLRRKERKLLEKCGLV
: ..: ...:D.R:: .EVLT IK..IKMY.W K.F.:.:::.R.:ER::LEK.G..
LTAYFRRKCVAATDDRVQKMNEVLTYIKFIKMYAWVKAFSQCVQKIREEERRILEKAGYF

QSLTSITLFIIPTVATAVWVLIHTSLKLKLTASMAFSMLASLNLLRLSVFFVPIAVKGLT
QS:T .. I: ..:A:.V . :H.:L ..LTA. .AF.::. .N :...: ..P.:VK.L:
QSITVGVAPIVVVIASVVTFSVHMTLGFDLTAAQAFTVVTVFNSMTFALKVTPFSVKSLS

NSKSAVMRFKKFFLQESPVFYVQTLQDPSKALVFEEATLSWQ------QTCPGIVNGALE
..: AV RFK..FL.FL.E. . ... ..P. .: .:.ATL:.W. Q::P :. . :
EASVAVDRFKSLFLMEEVHMIKNKPASPHIKIEMKNATLAWDSSHSSTQSSPKLTPKVKK

LERNGHASEGMTRP------RDALGPEEEGNSL------------GPELHKINLVVAMLS
:R . ..: .:R. . .A: .A: .E::G: L G..:H. :: .:..
DKRAPKGKKEKSRQLQHTEHQAVLAEQKGHLLLDSDERPSPEEEGKQIHAGSMRLQRTL
```

Fig. 7 (continued)

```
QHLYVLLGLQGMMLGVCGNTGSGKSSLLSAILEEMHLLEGSVGVQGSLAYVPQQAWIVSG
: :  :  :G.::G:CG:.GSGK:SL:SAIL :M LLEGS:.V.G:.AYV.QQAWI:: .
YNIDLEIE-EGKLVGICGSVGSGKTSLISAILGQMTLLEGSIAVSGTFAYVAQQAWILNA

NIRENILMGGAYDKARYLQVLHCCSLNRDLELLPFGDMTEIGERGLNLSGGQKQRISLAR
.:R:NIL.G .:D:.RY .VL:.C.L. DL:.LP .D:TEIGERG.NLSGGQ:QRISLAR
TLRDNILFGKEFDEERYNSVLNSCCLRPDLAILPNSDLTEIGERGANLSGGQRQRISLAR

AVYSDRQIYLLDDPLSAVDAHVGKHIFEECIKKTLRGKTVVLVTHQLYLEFCGQIILLE
A:YSDR.IY:LDDPLSA.:DAHVG.HIF...I:K.L:.KTV:.VTHQLYL  C.::I.::
ALYSDRSIYILDDPLSALDAHVGNHIFNSAIRKRLKSKTVLFVTHQLYLVDCDEVIFMK

NGKICENGTHSELMQKKGKYAQLIQKMHKEATSVSPAPLPSLPTVDARVLRACALSP---
.G I.E.GTH.ELM. .G.YA.:..:      L .:P.V:. . :..: S.
EGCITERGTHEELMNLNGDYATIFNNLL-------LGETPPVEINSKKEASGSQKSQ

--GHVAGHSKDSREAKVPEHQLTQEEEMEEGSLSWRVYHHYIQAAGGYMVSCIIFFFVVL
  G  .G. K...:.K  .E  QL.Q  EE.   :GS:.W.VY  YIQAAGG : . :I. ..:L
DKGPKPGSVKKEKAVKSEEGQLVQVEEKGQGSVPWSVYWVYIQAAGGPLAFLVIMVLFML

IVFLTIFSFWWLSYWLEQGSSGVSAMSRESNGTMADLGNIADNPQLSFYQLVYGLNALLI
 V   T.FS WWLSYW::QGSG S.. . :.::D  ::.DNP L.:Y. :Y.L.::::
NVGSTAFSTWWLSYWIKQGSGNSTVFEGNRSSVSD--SMRDNPFLQYYASIYALSMAVML
```

Fig. 7 (continued)

```
CVGVCSSGIFTKVTRKASTALHNKLFNKVFRCPMSFFDTIPIGRLLNCFAGDLEQLDQLL
: .... :F.K T :AS:.LH::LF.:::R.PM.FFDT.P.GR:LN F: D::::D L
ILKAIRGVVFVKGTLRASSRLHDELFRRILRSPMKFFDTTPTGRILNRFSKDMDEVDVRL

PIFSEQFLVLSLMVIAVLLIVSVLSPYILLMGAIIMVICFIYYMMFKKAIGVFKRLENYS
P. :E.F: ::V. .: .. :: P:.L:. .: . ::: . :I .KRL:N.:
PFQAEMFIQNVILVFFCVGMIAGVFPWFLVAVGPLLILFSVLHIVSRVLIRELKRLDNIT

RSPLFSHILNSLQGLSSIHVYGKTEDFISQFKRLTDAQNNYLLLFLSSTRWMALRLEIMT
:SP..SHI.::S:QGL::IH.Y.K.::F:.:::L.D .. ..LF..:.RW:A:RL::::
QSPFLSHITSSIQGLATIHAYNKRQEFLHRYQELLDDNQAPFFLFTCAMRWLAVRLDLIS

NLVTLAVALFVAFGISSTPYSFKVMAVNIVLQLASSFQATARIGLETEAQFTAVERILQY
.:..... ..P :::.A::..:QL.. FQ T.R:. ETEA:FT:VERI .Y
IALITTTGLMIVLMHGQIPSAYAGLAISYAVQLTGLFQFTVRLASETEARFTSVERINHY

MKMCVSEAPLHMEGTSCPQGWPQHGEIIFQDYHMKYRDNTPTVLHGINLTIRGHEVVGIV
:K.. EAP.::: P..WPQ.GEI.F:: M:YR:N.P.VL. ::.TI: .E :GIV
IKTLSLEAPARIKNKAPPHDWPQEGEITFENAEMRYRENLPLVLKKVSFTIKPKEKIGIV

GRTGSGKSSLGMALFRLVEPMAGRILIDGVDICSIGLEDLRSKLSVIPQDPVLLSGTIRF
GRTGSGKSSLGMALFRLVE ..G I IDGV I..IGL.DLRSKL::IPQ.:PVL.SGT:R
GRTGSGKSSLGMALFRLVELSGGCIKIDGVRISDIGLADLRSKLTIIPQEPVLFSGTVRS
```

Fig. 7 (continued)

```
NLDPFDRHTDQQIWDALERTFLTKAISKFPKKLHTDVVENGGNFSVGERQLLCIARAVLR
NLDPF:::T::QIWDALERT.:..I:..P KL:::V:ENG.NFSVGERQLLCIARA:LR
NLDPFNQYTEEQIWDALERTHMKECIAQLPLKLESEVMENGDNFSVGERQLLCIARALLR

NSKIILIDEATASIDMETDTLIQRTIREAFQGCTVLVIAHRVTTVLNCDHILVMGNGKVV
:.KI:::DEATA::D.ETD.LIQ.TIREAF..CT:L.IAHR: TVL..D.I:V:..G:VV
HCKILILDEATAAMDTETDLLIQETIREAFADCTMLTIAHRLHTVLGSDRIMVLAQGQVV

EFDRPEVLRKKPGSLFAALMATA      1345
EFD.P.VL ....S F A:.A.A
EFDTPSVLLSNDSSRFYAMCAAA      1428
```

Above, the bold lettering indicates the predicted transmembrane regions.

Fig. 8

The PROSITE: ATP/GTP-binding site motif A (P-loop) and
PROSITE: ABC transporters family signature motifs are
indicated in the HMMPFAM alignments below in bold and in
bold and underlined respectively.
HMMPFAM - alignment of LBRI_312_protein against pfam|hmm|ABC_tran
ABC transporter
This hit is scoring at : 143.2
Scoring matrix : BLOSUM62 (used to infer consensus pattern)

```
Q:  498 GMMLGVCGNTGSGKSSLLSAILEEMHLLEGSVGVQG-S----------LAYVP
        G :L:.G .G:GKS:LL..I  : .EG:: :.G .              :..V
H:    1 GevlalvGpNGaGKSTLLklisGllppteGtilldGardlrlsklkerlerlrkniqvvf Q:      QQAWIV---SGNIRENILMGGAY----DKARYLQVLHCCSLNRDLELLPFGDMTEIGERG
        Q.. :    .:RENI..G  .G  .:K...L  L. .....LE L.G  :..R
H:      Qdptlfpnveltvreniafglrlslglskdeqrarlkagaeellerlglgydhlldrrp Q:      LNLSGGQKQRISLARAVYSDRQIYLLDDPLSAVDAHVGKHIFEECIKKTLRGKTVLVTH
        .LSGGQKQR::..:ARA::..: ::.LLD:P.::D.  .:.E . . :G TV:L:TH
H:      gtLSGGqkQRvaiARaLltkpklllLDEPTaglDpasraqllellrelrqgggTvllitH Q:      QLQY-LEFCGQIILLENG             669
        .L.. :....I::LE:G
H:      dldlldrlaDrilvledG             198
```

Fig. 9

HMMPFAM - alignment of LBRI_312_protein against pfam|hmm|ABC_tran
ABC transporter
This hit is scoring at : 179.5
Scoring matrix : BLOSUM62 (used to infer consensus pattern)

```
Q:  1136 HEVVGIVGRTGSGKSSLGMALFRIVEPMAGRILIDG-VDICsIG-----LEDLRSKLSVI
              EV:.VG .G:GKS:L ..:  L:.P..G.IL:DG  D: :.    LE LR...:.V:
H:     1 GevlalvGpNGaGKSTLLkliisGllppteGtilldGardlr.lsklkerlerlrknigvv PQDPVLL---SGTIRFNLDPFDRH----TDQQIWDALERTFLTKAISKFPKKLHTDVVEN
         QDP.L.  .  T:R N:  R    : :  .L::  .::.::.  :       :  ..
         fQdptlfpnveltvreniafglrlslglsksdegrarlkkagaeellerlglgydhlldrr GGNFSVGERQLLCIARAVLRNSKIILIDEATASIDMETDTLIQRTIREAFQ-GCTVLVIA
         G..S G::Q ::IARA:L...K::L:DE.TA.:D  .: . ...:RE. Q G TVL:I..
         pgtLSGGqkQRvaiARaLltkpklllLDEPTagLDpasraqllelrelrqggTvllit HRVTTVLNCD-HILVMGNG                              1319
         H:::..   .ILV. :G
         HdldlldrlaDrilvledG                             198
```

Fig. 10

Below is information detailing the intron/exon boundaries in target #312. In bold is the stretch of highest confidence sequence.

AC007600 vs LBRI_312_DNA:

```
AC007600    25851  atgactaggaagaggacatactggtgtgcccaactcttctggtggcctcgt  25900
                   ||||||||||||||||||||||||||||||||||||||||||||||||||
LBRI_312_DNA    1  atgactaggaagaggacatactggtgtgcccaactcttctggtggcctcgt  50

AC007600    25901  gaatcgtggcatcgacataggcgatgacatggtttcaggacttatttatg  25949
                   |||||||||||||||||||||||||||||||||||||||||||||||||>
LBRI_312_DNA   51  gaatcgtggcatcgacataggcgatgacatggtttcaggacttatttat.  99

AC007600    25949  taag......cccagccccctggacaatgctggcctgttcctcctacctcac  29858
                   >>>> 3874 >>>>|||||||||||||||||||||||||||||||||
LBRI_312_DNA   99  ..........ccccctggacaatgctggcctgttcctcctacctcac  134

AC007600    29859  cgtgtcatggctcacccgctcatgatccaaagcttacggagtcgcttag  29908
                   |||||||||||||||||||||||||||||||||||||||||||||||||
LBRI_312_DNA  135  cgtgtcatggctcacccgctcatgatccaaagcttacggagtcgcttag  184

AC007600    29909  atgagaacaccatccctcactgtcagtccatgatgcctcagacaaaat  29958
                   ||||||||||||||||||||||||||||||||||||||||||||||||||
LBRI_312_DNA  185  atgagaacaccatccctcactgtcagtccatgatgcctcagacaaaaat  234
```

Fig. 10 (continued)

```
AC007600    29959  gtccaaggtgaa......tcaaggcttcaccgcctttgggaagaagaag  33368
                   ||||||||||||      |||||||||||||||||||||||||||||||
LBRI_312_DNA  235  .............>>>> 3376 >>>>|.........gcttcaccgcctttgggaagaagaag  268

AC007600    33369  tctcaaggcgagggattgaaaaagcttcagtgcttctggtgatgctgagg  33418
                   |||||||||||||||||||||||||||||||||||||||||||||||||
LBRI_312_DNA  269  tctcaaggcgagggattgaaaaagcttcagtgcttctggtgatgctgagg  318

AC007600    33419  ttccagagaacaaggttgatttcgatgcacttctgggcatctgcttctg  33468
                   ||||||||||||||||||||||||||||||||||||||||||||||||
LBRI_312_DNA  319  ttccagagaacaaggttgatttcgatgcacttctgggcatctgcttctg  368

AC007600    33469  cattgccagtgtactcgggccagtaag......tgtagatattgattata  34952
                   ||||||||||||||||||||||||||      |||||||||||||||||
LBRI_312_DNA  369  cattgccagtgtactcgggcca........>>>> 1450 >>>>|......atattgattata  402

AC007600    34953  ccaaagatcctggaatattcagaagagcagtggggaatgttgtccatgg  35002
                   |||||||||||||||||||||||||||||||||||||||||||||||||
LBRI_312_DNA  403  ccaaagatcctggaatattcagaagagcagtggggaatgttgtccatgg  452

AC007600    35003  agtgggactctgctttgccctttctctccgaatgtgaagtctcctga  35052
                   |||||||||||||||||||||||||||||||||||||||||||||||
LBRI_312_DNA  453  agtgggactctgctttgccctttctctccgaatgtgaagtctcctga  502
```

Fig. 10 (continued)

```
AC007600     35053  gtttctcctccagttggatcatcaaccaacgcacagccatcaggttccga  35102
                           ||||||||||||||||||||||||||||||||||||||||||||||||||
LBRI_312_DNA   503  gtttctcctccagttggatcatcaaccaacgcacagccatcaggttccga    552

AC007600     35103  gcagctgtttcctcctcctttgcctttgagaagctcatccaatttaagtctgt  35152
                           ||||||||||||||||||||||||||||||||||||||||||||||||||
LBRI_312_DNA   553  gcagctgtttcctcctcctttgcctttgagaagctcatccaatttaagtctgt    602

AC007600     35153  aatacacatcacctcaggagaggtaag......tgcaggccatcagcttc  41495
                           |||||||||||||||||||||||||||  6309 >>>>>|||||||||||
LBRI_312_DNA   603  aatacacatcacctcaggagagag...........gccatcagcttc         636

AC007600     41496  ttcaccggtgatgtaaactacctgtttgaaggggtgtgctatggaccct  41545
                           ||||||||||||||||||||||||||||||||||||||||||||||||||
LBRI_312_DNA   637  ttcaccggtgatgtaaactacctgtttgaaggggtgtgctatggaccct         686

AC007600     41546  agtactgatcacctgcgcatcgcgctgatcatccgctgtcatctgcagcattcttcctact  41595
                           ||||||||||||||||||||||||||||||||||||||||||||||||||
LBRI_312_DNA   687  agtactgatcacctgcgcatcgcgctgatcatccgctgtcatctgcagcattcttcctact    736

AC007600     41596  tcattattggatacactgcattattgccatcttatgctatctcctggtt  41645
                           ||||||||||||||||||||||||||||||||||||||||||||||||||
LBRI_312_DNA   737  tcattattggatacactgcattattgccatcttatgctatctcctggtt         786
```

Fig. 10 (continued)

```
AC007600   41646 ttcccactggcggtaat.....tccaggtattcatgacaagaatggctgt 42449
                 ||||||||||||||||     |||||||||||||||||||||||||||||
LBRI_312_DNA 787 ttcccactggcg..........>>>> 769 >>>>|gtattcatgacaagaatggctgt 821

AC007600   42450 gaaggctcagcatcacacatctgaggtcagcgcatccgtgtga 42499
                 |||||||||||||||||||||||||||||||||||||||||||
LBRI_312_DNA 822 gaaggctcagcatcacacatctgaggtcagcgcatccgtgtga 871

AC007600   42500 ccagtgaagttctcacttgcattaagctgattaaaatgtacacatgggag 42549
                 |||||||||||||||||||||||||||||||||||||||||||||||||
LBRI_312_DNA 872 ccagtgaagttctcacttgcattaagctgattaaaatgtacacatgggag 921

AC007600   42550 aaaccatttgcaaaaatcattgaaggtatg......cccagacctaagaag 42751
                 ||||||||||||||||||||||||||||        |||||||||||||
LBRI_312_DNA 922 aaaccatttgcaaaaatcattgaag............>>>> 167 >>>>|.........acctaagaag 956

AC007600   42752 gaaggaaaggaaactattggagaagtgcgggcttgtccagagcctgacaa 42801
                 ||||||||||||||||||||||||||||||||||||||||||||||||||
LBRI_312_DNA 957 gaaggaaaggaaactattggagaagtgcgggcttgtccagagcctgacaa 1006

AC007600   42802 gtataaccttgttcatcatcccacagtggccacagtggcctgggttctc 42851
                 |||||||||||||||||||||||||||||||||||||||||||||||||
LBRI_312_DNA 1007 gtataaccttgttcatcatcccacagtggccacagtggcctgggttctc 1056
```

Fig. 10 (continued)

```
AC007600    42852  atccacacatccttaaagctgaaactcacacagcgtcaatggtaag.........  42890
                          ||||||||||||||||||||||||||||||||||||||||>>>> 1330
LBRI_312_DNA 1057  atccacacatccttaaagctgaaactcacacagcgtcaatg...............  1095

AC007600    42890  tccaggccttcagcatgctggcctccttgaatctctccttcggtgtcagtg  44265
                          |||||||||||||||||||||||||||||||||||||||||||||||||||
LBRI_312_DNA 1095  .....gccttcagcatgctggcctccttgaatctctccttcggtgtcagtg  1140

AC007600    44266  ttctttgtgcctattgcagtcaaaggtctcacgaattccaagtctgcagt  44315
                          ||||||||||||||||||||||||||||||||||||||||||||||||||
LBRI_312_DNA 1141  ttctttgtgcctattgcagtcaaaggtctcacgaattccaagtctgcagt  1190

AC007600    44316  gatgaggttcaaggtagg......tacagaagttttcctccaggagagc  46592
                          ||||||||||||||>>>> 2243 |||||||||||||||||||||||||
LBRI_312_DNA 1191  gatgaggttcaag............aagttttcctccagcaaagctctggtctt  1224

AC007600    46593  cctgtttctatgtccagacattacaagaccccagcaaagctctggtctt  46642
                          ||||||||||||||||||||||||||||||||||||||||||||||||
LBRI_312_DNA 1225  cctgtttctatgtccagacattacaagaccccagcaaagctctggtctt  1274

AC007600    46643  tgaggaggccaccttgtcatggcaacagacctgtcccgggatcgtcaatg  46692
                          |||||||||||||||||||||||||||||||||||||||||||||||||
LBRI_312_DNA 1275  tgaggaggccaccttgtcatggcaacagacctgtcccgggatcgtcaatg  1324
```

Fig. 10 (continued)

```
AC007600   46693 gggcactggagctggagaggaacgggcatgcttctgaggggatgaccagg 46742
                 ||||||||||||||||||||||||||||||||||||||||||||||||||
LBRI_312_DNA 1325 gggcactggagctggagaggaacgggcatgcttctgaggggatgaccagg 1374

AC007600   46743 cctagagatgccctcgggccagagaaggaacagcctgggcccaga     46792
                 ||||||||||||||||||||||||||||||||||||||||||||| 
LBRI_312_DNA 1375 cctagagatgccctcgggccagagaaggaacagcctgggcccaga     1424

AC007600   46793 gttgcacaagatcaacctgtgtggtgtcca......gccagggctatgctg 49241
                 ||||||||||||||||||||||||||||||>>>> 2415 >>>>      
LBRI_312_DNA 1425 gttgcacaagatcaacctgtgtggt..........ggctatgctg     1458

AC007600   49242 tcccaacacttgtatgtcctccttggcttgcaggggatgatgttagggggt 49291
                 ||||||||||||||||||||||||||||||||||||||||||||||||||
LBRI_312_DNA 1459 tcccaacacttgtatgtcctccttggcttgcaggggatgatgttagggggt 1508

AC007600   49292 ctgcggcaacacgggggagtggtaagagcagcctgttgtcagccatcctgg 49341
                 ||||||||||||||||||||||||||||||||||||||||||||||||||
LBRI_312_DNA 1509 ctgcggcaacacgggggagtggtaagagcagcctgttgtcagccatcctgg 1558

AC007600   49342 aggaggtaag......cgcagatgcacttgctcgagggctcggtgggggt 52262
                 ||||||>>>> 2887 >>>>......atgcacttgctcgagggctcggtgggggt
LBRI_312_DNA 1559 aggag..........atgcacttgctcgagggctcggtgggggt      1592
```

Fig. 10 (continued)

```
AC007600    52263 gcagggaagcctgcctatgtcccccagcaggcctggatcgtcagcggga 52312
                  ||||||||||||||||||||||||||||||||||||||||||||||||
LBRI_312_DNA 1593 gcagggaagcctgcctatgtcccccagcaggcctggatcgtcagcggga 1642

AC007600    52313 acatcagggagaacatcctcatggaggcatatgacaaggcccgtaa... 52358
                  |||||||||||||||||||||||||||||||||||||||||||>>>>
LBRI_312_DNA 1643 acatcagggagaacatcctcatggaggcatatgacaaggcccg..... 1688

AC007600    52358 g......cacagatacctccaggtgctccactgctgctccctgaatcggg 54508
                  >  2112 >>>>|||||||||||||||||||||||||||||||||||||
LBRI_312_DNA 1688 .........atacctccaggtgctccactgctgctccctgaatcggg 1726

AC007600    54509 acctggaacttctgcccttggagacatgacagaggtgag......tgca 54543
                  |||||||||||||||||||||||||||||||||||||||  >>>>
LBRI_312_DNA 1727 acctggaacttctgcccttggagacatgacagag............. 1761

AC007600    54543 gattggagagcgggggcctcaacctctctgggggcagaaacagaggatca 57339
                  >  2747 >>>>||||||||||||||||||||||||||||||||||||||
LBRI_312_DNA 1761 .attggagagcgggggcctcaacctctctgggggcagaaacagaggatca 1810

AC007600    57340 gcctggccgcgccgtctattccgaccgtcagatctacctgctggacgac 57389
                  |||||||||||||||||||||||||||||||||||||||||||||||||
LBRI_312_DNA 1811 gcctggccgcgccgtcattccgaccgtcagatctacctgctggacgac 1860
```

Fig. 10 (continued)

```
AC007600   57390 cccctgtctgctgtgacgcccacgtggggaagcacattttgaggagtg 57439
                 ||||||||||||||||||||||||||||||||||||||||||||||||
LBRI_312_DNA 1861 cccctgtctgctgtgacgcccacgtggggaagcacattttgaggagtg 1910

AC007600   57440 cattaagaagacactcaggggggaagacgtcgtcctggtgaccaccagc 57489
                 ||||||||||||||||||||||||||||||||||||||||||||||||
LBRI_312_DNA 1911 cattaagaagacactcaggggggaagacgtcgtcctggtgaccaccagc 1960

AC007600   57490 tgcaggttag......tccagtacttagaattttgtggccagatcattt 59521
                 ||||||         ||||||||||||||||||||||||||||||||
                 ||||| >>>> 1998 >>>>|
LBRI_312_DNA 1961 tgcag.........tacttagaattttgtggccagatcattt 1994

AC007600   59522 gttggaaatgggaaaatctgtgaaaatggaactcacagtgagttaatgc 59571
                 ||||||||||||||||||||||||||||||||||||||||||||||||
LBRI_312_DNA 1995 gttggaaatgggaaaatctgtgaaaatggaactcacagtgagttaatgc 2044

AC007600   59572 agaaaaaggggaaatatgcccaacttatccagaagatgcacaaggaagcc 59621
                 ||||||||||||||||||||||||||||||||||||||||||||||||
LBRI_312_DNA 2045 agaaaaaggggaaatatgcccaacttatccagaagatgcacaaggaagcc 2094

AC007600   59622 acttcggtgagtcctgccccactgcccctcactacccacggtggacgcacg 59671
                 ||||||||||||||||||||||||||||||||||||||||||||||||
LBRI_312_DNA 2095 acttcggtgagtcctgccccactgcccctcactacccacggtggacgcacg 2144
```

Fig. 10 (continued)

```
AC007600    59672  tgtactcagggcctgtgctctctccccaggacatgttgcaggacacagca  59721
                   ||||||||||||||||||||||||||||||||||||||||||||||||||
LBRI_312_DNA 2145  tgtactcagggcctgtgctctctccccaggacatgttgcaggacacagca  2194

AC007600    59722  aagatagcagagaagccaaagtaga......cccagtgccggagcatca   61460
                   ||||||||||||||||||||||||| >>>> 1705 >>>> ||||||||
LBRI_312_DNA 2195  aagatagcagagaagccaaag.............tgccggagcatca    2228

AC007600    61461  gctcacacaggaggaggagatggaagaaggctccttgagttggagggtct  61510
                   ||||||||||||||||||||||||||||||||||||||||||||||||||
LBRI_312_DNA 2229  gctcacacaggaggaggagatggaagaaggctccttgagttggagggtct  2278

AC007600    61511  accaccactacatccaggcagctggaggtacg......cccaggttacat 63793
                   |||||||||||||||||||||||||||||||| >>>> 2249 >>>> ||
LBRI_312_DNA 2279  accaccactacatccaggcagctggag............gttacat    2312

AC007600    63794  ggtctcttgcataatttctcttcgtggtcgtgatcgtcttcttaacga   63843
                   ||||||||||||||||||||||||||||||||||||||||||||||||
LBRI_312_DNA 2313  ggtctcttgcataatttctcttcgtggtcgtgatcgtcttcttaacga   2362

AC007600    63844  tcttcagcttctgtggctggctactggttggagcagggctcggggtg    63893
                   ||||||||||||||||||||||||||||||||||||||||||||||
LBRI_312_DNA 2363  tcttcagcttctgtggctggctactggttggagcagggctcggggtg    2412
```

Fig. 10 (continued)

```
AC007600   63894  agtgccatgaggtgga......agcagccgagagagcaatggaaccatgg   65085
                  ||||||||||||||||     |||||||||||||||||||||||||
LBRI_312_DNA  2413  agtgccatgag...>>>> 1158 >>>>|.........ccgagagagcaatggaaccatgg   2446

AC007600   65086  cagacctgggcaacattgcagacaatcctcaactgtcctcctaccagctg   65135
                  ||||||||||||||||||||||||||||||||||||||||||||||||||
LBRI_312_DNA  2447  cagacctgggcaacattgcagacaatcctcaactgtcctcctaccagctg   2496

AC007600   65136  gtgtacgggctcaacgcgccctgctcctcatctgtgtgggtctgctcctc   65185
                  ||||||||||||||||||||||||||||||||||||||||||||||||||
LBRI_312_DNA  2497  gtgtacgggctcaacgcgccctgctcctcatctgtgtggggtctgctcctc   2546

AC007600   65186  agggattttcaccaaagtcacgaggaaggcatccacggccctgcacaaca   65235
                  ||||||||||||||||||||||||||||||||||||||||||||||||||
LBRI_312_DNA  2547  agggattttcaccaaagtcacgaggaaggcatccacggccctgcacaaca   2596

AC007600   65236  agctcttcaacaaggtatg......tgcaggttttccgctgcccatgag   70361
                  ||||||||||||||||||     |||||||||||||||||||||||
LBRI_312_DNA  2597  agctcttcaacaag...>>>> 5092 >>>>|.........gttttccgctgcccatgag   2630

AC007600   70362  tttctttgacaccatcccaataggccggctttgaactgcttcgcagggg   70411
                  |||||||||||||||||||||||||||||||||||||||||||||||||
LBRI_312_DNA  2631  tttctttgacaccatcccaataggccggctttgaactgcttcgcagggg   2680
```

Fig. 10 (continued)

```
AC007600    70412  acttgaacagctggaccagctcttgcccatctttcagagcagttcctg  70461
LBRI_312_DNA 2681  acttgaacagctggaccagctcttgcccatctttcagagcagttcctg  2730

AC007600    70462  gtcctgtccttaatggtgatcgccgtcctgttgattgtcagtgtgtc   70511
LBRI_312_DNA 2731  gtcctgtccttaatggtgatcgccgtcctgttgattgtcagtgtgtc   2780

AC007600    70512  tccatatatcctgttaatgggagccataatcatggttatttgcttcattt 70561
LBRI_312_DNA 2781  tccatatatcctgttaatgggagccataatcatggttatttgcttcattt 2830

AC007600    70562  attatatgtgag.....tgcaggatgttcaagaaggccatcggtgtgttc 70706
                   ||||||>>>>> 110 >>>>>.......gatgttcaagaaggccatcggtgtgttc
LBRI_312_DNA 2831  attatat.....                                       2865

AC007600    70707  aagagactggagaactatagcggtcctccttattctcccacatccctcaa 70756
LBRI_312_DNA 2866  aagagactggagaactatagcggtcctccttattctcccacatccctcaa 2915

AC007600    70757  ttctctgcaaggcctgagctccatgtctatggaaaactgaagact      70806
LBRI_312_DNA 2916  ttctctgcaaggcctgagctccatgtctatggaaaactgaagact      2965
```

Fig. 10 (continued)

```
AC007600   70807 tcatcagccagtgag......ctcaggtttaagagggctgactgatgcgca  73166
                 ||||||||||||||   >>>>> 2326 >>>>> |||||||||||||||||||||
LBRI_312_DNA 2966 tcatcagcca..................gtttaagagggctgactgatgcgca 2999

AC007600   73167 gaataactacctgctgtttctatcttccacacgatggcattga  73216
                 |||||||||||||||||||||||||||||||||||||||||||
LBRI_312_DNA 3000 gaataactacctgctgtttctatcttccacacgatggcattga 3049

AC007600   73217 ggctggagatcatgaccaacctgtgacctggctgttgccctgttcgtg  73266
                 ||||||||||||||||||||||||||||||||||||||||||||||||
LBRI_312_DNA 3050 ggctggagatcatgaccaacctgtgacctggctgttgccctgttcgtg 3099

AC007600   73267 gcttttggcatttcctccacccctactcctttaaagtcatggctgtcaa  73316
                 |||||||||||||||||||||||||||||||||||||||||||||||||
LBRI_312_DNA 3100 gcttttggcatttcctccacccctactcctttaaagtcatggctgtcaa 3149

AC007600   73317 catcgtgctgcaggtgag......tctagctggcgtccagcttccaggcc  79103
                 ||||||||||||||   >>>> 5753 >>>>|||||||||||||||||||
LBRI_312_DNA 3150 catcgtgctgcag................ctggcgtccagcttccaggcc 3183

AC007600   79104 actgcccggattggcttggagacagaggcacagttcacggctgtagagag  79153
                 ||||||||||||||||||||||||||||||||||||||||||||||||||
LBRI_312_DNA 3184 actgcccggattggcttggagacagaggcacagttcacggctgtagagag 3233
```

Fig. 10 (continued)

```
AC007600   79154  gatactgcagtacatgaaggtggg......acaagatgtgtctcggaa      80670
                  ||||||||||||||||||||||||      ||||||||||||||||||
LBRI_312_DNA 3234 gatactgcagtacatgaag.........>>>>> 1483 >>>>>|atgtgtctcggaa  3267

AC007600   80671  gctcctttacacatggaaggcacaagttgtcccagggtggccacagca     80720
                  ||||||||||||||||||||||||||||||||||||||||||||||||
LBRI_312_DNA 3268 gctcctttacacatggaaggcacaagttgtcccagggtggccacagca     3317

AC007600   80721  tggggaaatcatatttcaggattatcacatgaaatacagagacaacacac   80770
                  ||||||||||||||||||||||||||||||||||||||||||||||||||
LBRI_312_DNA 3318 tggggaaatcatatttcaggattatcacatgaaatacagagacaacacac   3367

AC007600   80771  ccacgtgcttcacggcatcaacctgaccatccgcggccacgaagtggtg    80820
                  |||||||||||||||||||||||||||||||||||||||||||||||||
LBRI_312_DNA 3368 ccacgtgcttcacggcatcaacctgaccatccgcggccacgaagtggtg    3417

AC007600   80821  ggcatcgtgggaaggacgggctctggtgag......cacagggaagtcct   82360
                  |||||||||||||||||||||||||||||      |||||||||||
LBRI_312_DNA 3418 ggcatcgtgggaaggacgggctctg.........>>>>> 1506 >>>>>|......ggaagtcct  3451

AC007600   82361  ccttgggcatggctctcttccgctggtggagccatggcaggccggatt     82410
                  ||||||||||||||||||||||||||||||||||||||||||||||||
LBRI_312_DNA 3452 ccttgggcatggctctcttccgctggtggagccatggcaggccggatt     3501
```

Fig. 10 (continued)

```
AC007600   82411  ctcattgacggcgtggacatttgcagcatcggcctggaggacttgcggtc  82460
                  ||||||||||||||||||||||||||||||||||||||||||||||||||
LBRI_312_DNA 3502 ctcattgacggcgtggacatttgcagcatcggcctggaggacttgcggtc  3551

AC007600   82461  caagctctcagtgatccctcaagatccagtgctgctctcaggaaccatca  82510
                  ||||||||||||||||||||||||||||||||||||||||||||||||||
LBRI_312_DNA 3552 caagctctcagtgatccctcaagatccagtgctgctctcaggaaccatca  3601

AC007600   82511  ggtgag......ggtagattcaacctagatcccttttgaccgtcacactga  86834
                  |>>>>> 4290 >>>>>|||||||||||||||||||||||||||||||||
LBRI_312_DNA 3602 g...........attcaacctagatcccttttgaccgtcacactga  3635

AC007600   86835  ccagcagatctgggatgccttggagaggacattcctgaccaaggccgtaa  86880
                  ||||||||||||||||||||||||||||||||||||||||||||>>>>>
LBRI_312_DNA 3636 ccagcagatctgggatgccttggagaggacattcctgaccaaggcc....  3681

AC007600   86880  g......cgcagatctcaaagttcccaaaaagctgcatacagatgtggtg  87589
                  |>>>>> 670 >>>>>|||||||||||||||||||||||||||||||||
LBRI_312_DNA 3681 ........atctcaaagttcccaaaaagctgcatacagatgtggtg  3720

AC007600   87590  gaaaacggtggaaacttctctgtggggagagcagctgctctgcattgc  87639
                  ||||||||||||||||||||||||||||||||||||||||||||||||
LBRI_312_DNA 3721 gaaaacggtggaaacttctctgtggggagagcagctgctctgcattgc  3770
```

Fig. 10 (continued)

```
AC007600    87640  cagggctgtgcttcgcaactccaaggtgag......atcagatcatcctt  90117
                   ||||||||||||||||||||||||||||||       |||||||||||||
LBRI_312_DNA 3771  cagggctgtgcttcgcaactccaag|>>>> 2444 >>>>......atcatcctt  3804

AC007600    90118  atcgatgaagccacagccctccattgacatggagacagacccctgatcca  90167
                   ||||||||||||||||||||||||||||||||||||||||||||||||||
LBRI_312_DNA 3805  atcgatgaagccacagccctccattgacatggagacagacccctgatcca  3854

AC007600    90168  gcgcacaatccgtgaagccttccagggctgcaccgtgctcgtcattgccc  90217
                   ||||||||||||||||||||||||||||||||||||||||||||||||||
LBRI_312_DNA 3855  gcgcacaatccgtgaagccttccagggctgcaccgtgctcgtcattgccc  3904

AC007600    90218  accgtgtcaccactgtgctgaactgtgaccacatcctggttatgggcaat  90267
                   ||||||||||||||||||||||||||||||||||||||||||||||||||
LBRI_312_DNA 3905  accgtgtcaccactgtgctgaactgtgaccacatcctggttatgggcaat  3954

AC007600    90268  gggaaggtgaa......tccaggtggtagaatttgatcggccggaggtact  90431
                   |||||||||||       |||||||||||||||||||||||||||||||
LBRI_312_DNA 3955  gggaag......|>>>> 129 >>>>......gtggtagaatttgatcggccggaggtact  3989

AC007600    90432  gcggaagaagcctgggtcattgttcgcagccctcatggccacagcc  90477
                   ||||||||||||||||||||||||||||||||||||||||||||||
LBRI_312_DNA 3990  gcggaagaagcctgggtcattgttcgcagccctcatggccacagcc  4035
```

REGULATION OF HUMAN MRP5-LIKE PROTEIN

This application is a National Stage application of co-pending PCT application PCT/EP02/02554 filed Mar. 8, 2002, which was published in English under PCT Article 21(2) on Sep. 19, 2002, which claims the benefit of U.S. provisional application Ser. No. 60/274,233 filed Mar. 9, 2001 and Ser. No. 60/323,334 filed Sep. 20, 2001. These applications are incorporated herein by reference in their entireties.

TECHNICAL FIELD OF THE INVENTION

The invention relates to the area of membrane transport protein regulation. More particularly, it relates to the area of human ABC transporters and their regulation.

BACKGROUND OF THE INVENTION

The ATP-binding cassette (ABC) transporters, also called the "traffic ATPases," comprise a superfamily of over 100 membrane proteins that mediate transport and channel functions in prokaryotes and eukaryotes (See Higgins, C. F. (1992) Annu. Rev. Cell Biol. 8:67–113, and U.S. Pat. Nos. 5,858,719 and 6,030,806). ABC transporters share a similar overall structure and significant sequence homology. Typically ABC transporters have four conserved domains, two hydrophobic domains which may impart substrate specificity (Payne et al., Mol. Gen. Genet. 200:493–496, 1985; Foote et al., Nature 345:255–258, 1990; Anderson et al., Science 253:202–205, 1991; Shustik et al., Br. J. Haematol. 79:50–56, 1991; Covitz et al., EMBO J. 13:1752–1759, 1994), and two highly conserved domains associated with ATP binding and hydrolysis (Higgins, supra). ABC transporters govern unidirectional transport of molecules into or out of cells and across subcellular membranes (Higgins, supra). Their substrates range from heavy metals (Ouellette et al., Res. Microbiol. 142:737–746 1991) to peptides and full size proteins (Gartner et al., Nature Genet. 1:16–23 1992).

Eukaryotic ABC transporter proteins include: P-glycoproteins, also known as multidrug resistance (MDR) proteins, which are associated with resistance to a wide range of hydrophobic drugs (MDR1; Gottesman, M. M. & Pastan, I. (1993) Annu. Rev. Biochem. 62:385–427) or with phosphatidylcholine transport (MDR2; Ruetz, S. & Gros, P. (1994) Cell 77:1071–1081); CFTR, the cystic fibrosis transmembrane conductance regulator (Welsh, M. J. & Smith, A. E. (1993) Cell 73:1251–1254); TAP proteins, the transporters associated with antigen processing in mammalian cells (Androlewicz, M. J. et al. (1994) Proc. Natl. Acad. Sci. USA 91:12716–12720); cMOAT/cMRP1, which is associated with transport of glutathione, glucuronide, and sulfate conjugates across the canalicular membrane (Buchler, M. et al. (1996) J. Biol. Chem. 271:15091–15098); and STE6, which exports the a-factor mating pheromone of S. cerevisiae (Michaelis, S. (1993) Semin. Cell Biol. 4:17–27). Prokaryotic ABC proteins include periplasmic nutrient permeases, such as those responsible for uptake of maltose (MalFGK) and histidine (HisMPQ) in gram-negative bacteria, and toxin exporters such as those required for export of hemolysin (HlyB) and colicin (ColV) from E. coli (Higgins, supra). See U.S. Pat. No. 5,858,719.

Because of the important biological effects of ABC transporters, there is a need in the art to identify additional members of the ABC transporter family whose activity can be regulated to provide therapeutic effects.

SUMMARY OF THE INVENTION

It is an object of the invention to provide reagents and methods of regulating a human MRP5-like protein. This and other objects of the invention are provided by one or more of the embodiments described below.

One embodiment of the invention is a MRP5-like protein polypeptide comprising an amino acid sequence selected from the group consisting of:

amino acid sequences which are at least about 41% identical to the amino acid sequence shown in SEQ ID NO: 2; and the amino acid sequence shown in SEQ ID NO: 2.

Yet another embodiment of the invention is a method of screening for agents which decrease extracellular matrix degradation. A test compound is contacted with a MRP5-like protein polypeptide comprising an amino acid sequence selected from the group consisting of:

amino acid sequences which are at least about 41% identical to the amino acid sequence shown in SEQ ID NO: 2; and the amino acid sequence shown in SEQ ID NO: 2

Binding between the test compound and the MRP5-like protein polypeptide is detected. A test compound which binds to the MRP5-like protein polypeptide is thereby identified as a potential agent for decreasing extracellular matrix degradation. The agent can work by decreasing the activity of the MRP5-like protein.

Another embodiment of the invention is a method of screening for agents which decrease extracellular matrix degradation. A test compound is contacted with a polynucleotide encoding a MRP5-like protein polypeptide, wherein the polynucleotide comprises a nucleotide sequence selected from the group consisting of:

nucleotide sequences which are at least about 50% identical to the nucleotide sequence shown in SEQ ID NO: 1; and the nucleotide sequence shown in SEQ ID NO: 1

Binding of the test compound to the polynucleotide is detected. A test compound which binds to the polynucleotide is identified as a potential agent for decreasing extracellular matrix degradation. The agent can work by decreasing the amount of the MRP5-like protein through interacting with the MRP5-like protein mRNA.

Another embodiment of the invention is a method of screening for agents which regulate extracellular matrix degradation. A test compound is contacted with a MRP5-like protein polypeptide comprising an amino acid sequence selected from the group consisting of:

amino acid sequences which are at least about 41% identical to the amino acid sequence shown in SEQ ID NO: 2;

the amino acid sequence shown in SEQ ID NO: 2

A MRP5-like protein activity of the polypeptide is detected. A test compound which increases MRP5-like protein activity of the polypeptide relative to MRP5-like protein activity in the absence of the test compound is thereby identified as a potential agent for increasing extracellular matrix degradation. A test compound which decreases MRP5-like protein activity of the polypeptide relative to MRP5-like protein activity in the absence of the test compound is thereby identified as a potential agent for decreasing extracellular matrix degradation.

Even another embodiment of the invention is a method of screening for agents which decrease extracellular matrix degradation. A test compound is contacted with a MRP5-like protein product of a polynucleotide which comprises a nucleotide sequence selected from the group consisting of:

nucleotide sequences which are at least about 50% identical to the nucleotide sequence shown in SEQ ID NO: 1; and the nucleotide sequence shown in SEQ ID NO: 1

Binding of the test compound to the MRP5-like protein product is detected. A test compound which binds to the MRP5-like protein product is thereby identified as a potential agent for decreasing extracellular matrix degradation.

Still another embodiment of the invention is a method of reducing extracellular matrix degradation. A cell is contacted with a reagent which specifically binds to a polynucleotide encoding a MRP5-like protein polypeptide or the product encoded by the polynucleotide, wherein the polynucleotide comprises a nucleotide sequence selected from the group consisting of:

nucleotide sequences which are at least about 50% identical to the nucleotide sequence shown in SEQ ID NO: 1; and the nucleotide sequence shown in SEQ ID NO: 1.

MRP5-like protein activity in the cell is thereby decreased.

The invention thus provides a human MRP5-like protein that can be used to identify test compounds that may act, for example, as activators or inhibitors of the protein's activity. Human MRP5-like protein and fragments thereof also are useful in raising specific antibodies that can block the protein and effectively reduce its activity.

BRIEF DESCRIPTION OF THE DRAWINGS

FIG. 1 shows the DNA-sequence encoding a MRP5-like protein Polypeptide (SEQ ID NO: 1).

FIG. 2 shows the amino acid sequence deduced from the DNA-sequence of FIG. 1 (SEQ ID NO: 2).

FIG. 3 shows the amino acid sequence of the protein identified by swissnew|Q9QYM0|MRP5_RAT (SEQ ID NO: 3).

FIG. 4 shows the DNA-sequence encoding a MRP5-like protein Polypeptide (SEQ ID NO: 4).

FIG. 5 shows the DNA-sequence encoding a MRP5-like protein Polypeptide (SEQ ID NO: 5).

FIG. 6 shows the DNA-sequence encoding a MRP5-like protein Polypeptide (SEQ ID NO: 6).

FIG. 7 shows the BLASTP—alignment of LBRI_312_protein (SEQ ID NO: 2) against swissnew|Q9QYM0|MRP5_RAT (SEQ ID NO: 3).

FIG. 8 shows the HMMPFAM—alignment of LBRI_312_protein (SEQ ID NO: 2) against pfam|hmm|ABC_tran ABC transporter.

FIG. 9 shows the HMMPFAM—alignment of LBRI_312_protein (SEQ ID NO: 2) against pfam|hmm|ABC_tran ABC transporter.

FIG. 10 shows the Intron/exon boundaries.

DETAILED DESCRIPTION OF THE INVENTION

Figure 11:
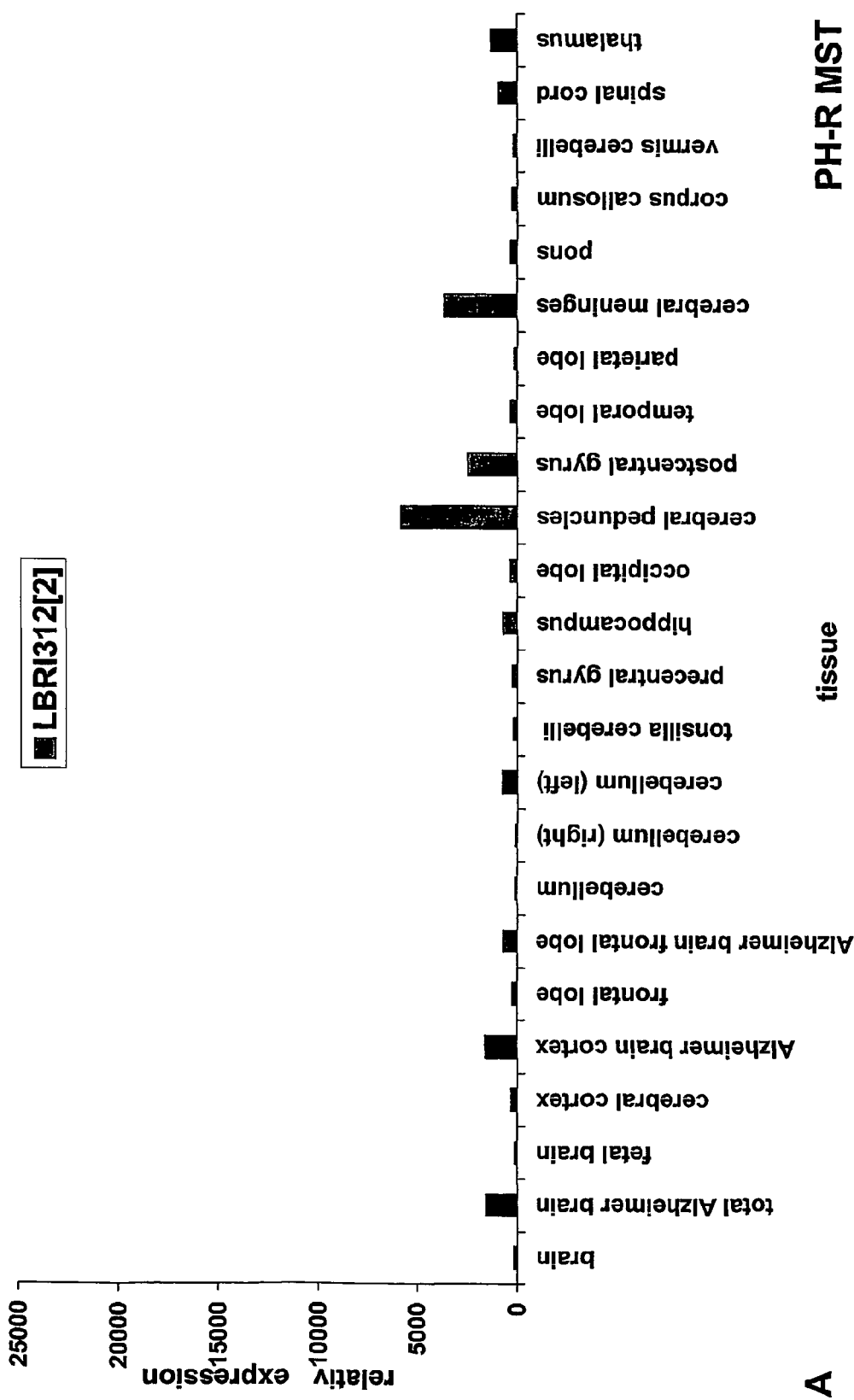
FIG. 11 shows the Expression profiling of MRP5-like protein

The invention relates to an isolated polynucleotide from the group consisting of:

a) a polynucleotide encoding a heparanase-like enzyme polypeptide comprising an amino acid sequence selected from the group consisting of:
  amino acid sequences which are at least about 41% identical to the amino acid sequence shown in SEQ ID NO: 2; and
  the amino acid sequence shown in SEQ ID NO: 2
b) a polynucleotide comprising the sequence of SEQ ID NO: 1;
c) a polynucleotide which hybridizes under stringent conditions to a polynucleotide specified in (a) and (b) and encodes a heparanase-like enzyme polypeptide;
d) a polynucleotide the sequence of which deviates from the polynucleotide sequences specified in (a) to (c) due to the degeneration of the genetic code and encodes a heparanase-like enzyme polypeptide; and
e) a polynucleotide which represents a fragment, derivative or allelic variation of a polynucleotide sequence specified in (a) to (d) and encodes a heparanase-like enzyme polypeptide.

Furthermore, it has been discovered by the present applicant that a novel MRP5-like protein, particularly a human MRP5-like protein, can be used in therapeutic methods to treat a cardiovascular disorder, cancer or a CNS disorder.

Human MRP5-like protein comprises the amino acid sequence shown in SEQ ID NO: 2. A coding sequence for human MRP5-like protein is shown in SEQ ID NO: 1. This sequence is located on chromosome 16. Related ESTs (SEQ ID NOS: 4–6) are expressed in mammary gland, colon, and adenocarcinoma.

Human MRP5-like protein is 40% identical over 1343 amino acids to swissnew|Q9QYM0|MRP5_RAT (SEQ ID NO: 3) (FIG. 1). BLOCKS, HMMPFAM, and Prosite searches identified the ABC transporter region signature domains in SEQ ID NO: 2. Additionally, HMMPFAM and Prosite identified ATP-binding domains, which are found in ABC transporters.

Human MRP5-like protein of the invention is expected to be useful for the same purposes as previously identified multidrug resistance proteins. Human MRP5-like protein is believed to be useful in therapeutic methods to treat disorders such as cardiovascular disorders, cancer, and CNS disorders. Human MRP5-like protein also can be used to screen for human MRP5-like protein activators and inhibitors.

Polypeptides

Human MRP5-like protein polypeptides according to the invention comprise at least 6, 10, 15, 20, 25, 50, 75, 100, 125, 150, 175, 200, 225, 250, 275, 300, 325, 350, 375, 400, 425, 450, 475, 500, 600, 700, 800, 900, 1000, 1100, 1200, 1300, or 1345 contiguous amino acids selected from the amino acid sequence shown in SEQ ID NO: 2 or a biologically active variant thereof, as defined below. An MRP5-like polypeptide of the invention therefore can be a portion of an MRP5-like protein, a full-length MRP5-like protein, or a fusion protein comprising all or a portion of an MRP5-like protein.

Biologically Active Variants

Human MRP5-like protein polypeptide variants that are biologically active, e.g., retain the ability to export toxins, therapeutic agents, or metabolic compounds such as cGMP, also are MRP5-like protein polypeptides. Preferably, naturally or non-naturally occurring MRP5-like protein polypeptide variants have amino acid sequences which are at least about 41, 45, 50, 55, 60, 65, or 70, preferably about 75, 80, 85, 90, 96, 96, 98, or 99% identical to the amino acid sequence shown in SEQ ID NO: 2 or a fragment thereof. Percent identity between a putative MRP5-like protein polypeptide variant and an amino acid sequence of SEQ ID NO: 2 is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). Those skilled in the art appreciate that there are many established algorithms available to align two amino acid sequences. The "FASTA"similarity search algorithm of Pearson and Lipman is a suitable protein alignment method for examining the level of identity shared by an amino acid sequence disclosed herein and the amino acid sequence of a putative variant. The FASTA algorithm is described y Pearson and Lipman, Proc. Nat'l Acad. Sci. USA 85:2444(1988), and by Pearson, Meth. Enzymol. 183:63 (1990). Briefly, FASTA first characterizes sequence similarity by identifying regions shared by the query sequence (e.g. SEQ ID NO: 2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to for man approximate alignment with gaps.

Finally, the highest scoring regions of the two amino acid sequences are aligned using a modification of the Needleman-Wunsch-Sellers algorithm (Needleman and Wunsch, J. Mol. Biol.48:444 (1970); Sellers, SIAM J. Appl. Math. 26:787 (1974)), which allows for amino acid insertions and deletions. Preferred parameters for FASTA analysis are: ktup=1, gapopeningpenalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990). FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of an MRP5-like protein polypeptide can be found using computer programs well known in the art, such as DNASTAR software. Whether an amino acid change results in a biologically active MRP5-like protein polypeptide can readily be determined by assaying for transport activities. For example, transport of therapeutic agents can be assessed, e.g., as described in Wijnholds et al., Proc. Natl. Acad. Sci. U.S.A. 97, 7476–81, 2000. Transport of cGMP can be assessed, e.g., as described in Jedlitchsky et al., J. Biol. Chem. 275, 30069–74, 2000.

Fusion Proteins

Fusion proteins are useful for generating antibodies against MRP5-like protein polypeptide amino acid sequences and for use in various assay systems. For example, fusion proteins can be used to identify proteins that interact with portions of an MRP5-like protein polypeptide. Protein affinity chromatography or library-based assays for protein-protein interactions, such as the yeast two-hybrid or phage display systems, can be used for this purpose. Such methods are well known in the art and also can be used as drug screens.

AN MRP5-like protein polypeptide fusion protein comprises two polypeptide segments fused together by means of a peptide bond. The first polypeptide segment comprises at least 6, 10, 15, 20, 25, 50, 75, 100, 125, 150, 175, 200, 225, 250, 275, 300, 325, 350, 375, 400, 425, 450, 475, 500, 600, 700, 800, 900, 1000, 1100, 1200, 1300, or 1345 contiguous amino acids of SEQ ID NO: 2 or of a biologically active variant, such as those described above. The first polypeptide segment also can comprise full-length MRP5-like protein The second polypeptide segment can be a fill-length protein or a protein fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the MRP5-like protein polypeptide-encoding sequence and the heterologous protein sequence, so that the MRP5-like protein polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NO: 1 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human MRP5-like protein polypeptide can be obtained using MRP5-like protein polypeptide polynucleotides (described below) to make suitable probes or primers for screening cDNA expression libraries from other species, such as mice, monkeys, or yeast, identifying cDNAs which encode homologs of MRP5-like protein polypeptide, and expressing the cDNAs as is known in the art.

Polynucleotides

AN MRP5-like protein polynucleotide can be single- or double-stranded and comprises a coding sequence or the complement of a coding sequence for an MRP5 -like protein polypeptide. A coding sequence for human MRP5-like protein is shown in SEQ ID NO: 1.

Degenerate nucleotide sequences encoding human MRP5-like protein polypeptides, as well as homologous nucleotide sequences which are at least about 50, 55, 60, 65, 70, preferably about 75, 90, 96, 98, or 99% identical to the nucleotide sequence shown in SEQ ID NO: 1 or its complement also are MRP5-like protein polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of MRP5-like protein polynucleotides that encode biologically active MRP5-like protein polypeptides also are MRP5-like protein polynucleotides. Polynucleotide fragments comprising at least 8, 9, 10, 11, 12, 15, 20, or 25 contiguous nucleotides of SEQ ID NO: 1 or its complement also are MRP5-like protein polynucleotides. These fragments can be used, for example, as hybridization probes or as antisense oligonucleotides.

Identification of Polynucleotide Variants and Homologs

Variants and homologs of the MRP5-like protein polynucleotides described above also are MRP5-like protein polynucleotides. Typically, homologous MRP5-like protein polynucleotide sequences can be identified by hybridization of candidate polynucleotides to known MRP5-like protein polynucleotides under stringent conditions, as is known in the art. For example, using the following wash conditions— 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the MRP5-like protein polynucleotides disclosed herein also can be identified by making suitable probes or primers and screening cDNA expression libraries from other species, such as mice, monkeys, or yeast. Human variants of MRP5-like protein polynucleotides can be identified, for example, by screening human cDNA expression libraries. It is well known that the $T_m$ of a double-stranded DNA decreases by 1–1.5° C. with every 1% decrease in homology (Bonner et al., J. Mol. Biol. 81, 123 (1973). Variants of human MRP5-like protein polynucleotides or MRP5-like protein polynucleotides of other species can therefore be identified by hybridizing a putative homologous MRP5-like protein polynucleotide with a polynucleotide having a nucleotide sequence of SEQ ID NO: 1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to MRP5-like protein polynucleotides or their complements following stringent hybridization and/or wash conditions also are MRP5-like protein polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between an MRP5-like protein polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m = 81.5° C. - 16.6(\log_{10}[Na^+]) + 0.41(\% \ G+C) - 0.63(\% \ \text{formamide}) - 600/l)$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

AN MRP5-like protein polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated MRP5-like protein polynucleotides. For example, restriction enzymes and probes can be used to isolate polynucleotide fragments, which comprise MRP5-like protein nucleotide sequences. Isolated polynucleotides are in preparations that are free or at least 70, 80, or 90% free of other molecules.

Human MRP5-like protein cDNA molecules can be made with standard molecular biology techniques, using MRP5-like protein mRNA as a template. Human MRP5-like protein cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesize MRP5-like protein polynucleotides. The degeneracy of the genetic code allows alternate nucleotide sequences to be synthesized which will encode an MRP5-like protein polypeptide having, for example, an amino acid sequence shown in SEQ ID NO: 2 or a biologically active variant thereof.

Extending Polynucleotides

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) that are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA that might be present in limited amounts in a particular sample.

Obtaining Polypeptides

Human MRP5-like protein polypeptides can be obtained, for example, by purification from human cells, by expression of MRP5-like protein polynucleotides, or by direct chemical synthesis.

Protein Purification

Human MRP5-like protein polypeptides can be purified from any cell that expresses the polypeptide, including host cells that have been transfected with MRP5-like protein expression constructs. A purified MRP5-like protein polypeptide is separated from other compounds that normally associate with the MRP5-like protein polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified MRP5-like protein polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express an MRP5-like protein polynucleotide, the polynucleotide can be inserted into an expression vector that contains the necessary elements for the transcription and translation of the inserted coding sequence. Methods that are well known to those skilled in the art can be used to construct expression vectors containing sequences encoding MRP5-like protein polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding an MRP5-like protein polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding an MRP5-like protein polypeptide, vectors based on SV40 or EBV can be used with an appropriate selectable marker.

Bacterial and Yeast Expression Systems

In bacterial systems, a number of expression vectors can be selected depending upon the use intended for the MRP5-like protein polypeptide. For example, when a large quantity of an MRP5-like protein polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding the MRP5-like protein polypeptide can be ligated into the vector in frame with sequences for the amino-terminal Met and the subsequent 7 residues of β-galactosidase so that a hybrid protein is produced. pIN vectors (Van Heeke & Schuster, *J. Biol. Chem.* 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding MRP5-like protein polypeptides can be driven by any of a number of promoters. For example, viral promoters such as the $^{35}$S and 19S promoters of CaMV can be used alone or in combination with the omega leader sequence from TMV (Takamatsu, *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (e.g., Hobbs or Murray, in McGRAW HILL YEARBOOK OF SCIENCE AND TECHNOLOGY, McGraw Hill, New York, N.Y., pp. 191–196, 1992).

An insect system also can be used to express an MRP5-like protein polypeptide. For example, in one such system *Autographa californica* nuclear polyhedrosis virus (AcNPV) is used as a vector to express foreign genes in *Spodoptera frugiperda* cells or in *Trichoplusia larvae*. Sequences encoding MRP5-like protein polypeptides can be cloned into a non-essential region of the virus, such as the polyhedrin gene, and placed under control of the polyhedrin promoter. Successful insertion of MRP5-like protein polypeptides will render the polyhedrin gene inactive and produce recombinant virus lacking coat protein. The recombinant viruses can then be used to infect *S. frugiperda* cells or *Trichoplusia larvae* in which MRP5-like protein polypeptides can be expressed (Engelhard et al., *Proc. Nat. Acad. Sci.* 91, 3224–3227, 1994).

Mammalian Expression Systems

A number of viral-based expression systems can be used to express MRP5-like protein polypeptides in mammalian host cells. For example, if an adenovirus is used as an expression vector, sequences encoding MRP5-like protein polypeptides can be ligated into an adenovirus transcription/translation complex comprising the late promoter and tripartite leader sequence. Insertion in a non-essential E1 or E3 region of the viral genome can be used to obtain a viable virus that is capable of expressing an MRP5-like protein polypeptide in infected host cells (Logan & Shenk, *Proc. Natl. Acad. Sci.* 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g. liposomes, polycationic amino polymers, or vesicles).

Specific initiation signals also can be used to achieve more efficient translation of sequences encoding MRP5-like protein polypeptides. Such signals include the ATG initiation codon and adjacent sequences. In cases where sequences encoding an MRP5-like protein polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125–162, 1994).

Host Cells

A host cell strain can be chosen for its ability to modulate the expression of the inserted sequences or to process the expressed MRP5-like protein polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells that have specific cellular machinery and characteristic mechanisms for post-translational: activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express MR5-like protein polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced MRP5-like protein sequences. Resistant clones of stably transformed cells can be proliferated using tissue culture techniques appropriate to the cell type. See, for example, ANIMAL CELL CULTURE, R. I. Freshney, ed., 1986.

Any number of selection systems can be used to recover transformed cell lines.

These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980) genes which can be employed in tk⁻ or aprt⁻ cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567–70, 1980), npt confers resistance to the aminoglycosides, neomycin and G418 (Colbere-Garapin et al., *J. Mol. Biol.* 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, *Proc. Natl. Acad. Sci.* 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression

Although the presence of marker gene expression suggests that the MRP5-like protein polynucleotide is also present, its presence and expression may need to be confirmed. For example, if a sequence encoding an MRP5-like protein polypeptide is inserted within a marker gene sequence, transformed cells containing sequences that encode an MRP5-like protein polypeptide can be identified by the absence of marker gene function. Alternatively, a marker gene can be placed in tandem with a sequence encoding an MRP5-like protein polypeptide under the control of a single promoter. Expression of the marker gene in response to induction or selection usually indicates expression of the MRP5-like protein polynucleotide.

Alternatively, host cells which contain an MRP5-like protein polynucleotide and which express an MRP5-like protein polypeptide can be identified by a variety of procedures known to those of skill in the art. These procedures include, but are not limited to, DNA-DNA or DNA-RNA hybridizations and protein bioassay or immunoassay techniques that include membrane, solution, or chip-based technologies for the detection and/or quantification of nucleic acid or protein. For example, the presence of a polynucleotide sequence encoding an MRP5-like protein polypeptide can be detected by DNA-DNA or DNA-RNA hybridization or amplification using probes or fragments or fragments of polynucleotides encoding an MRP5-like protein polypeptide. Nucleic acid amplification-based assays involve the use of oligonucleotides selected from sequences encoding an MRP5-like protein polypeptide to detect transformants that contain an MRP5-like protein polynucleotide.

A variety of protocols for detecting and measuring the expression of an MRP5-like protein polypeptide, using either polyclonal or monoclonal antibodies specific for the polypeptide, are known in the art. Examples include enzyme-inked immunosorbent assay (ELISA), radioimmunoassay (RIA), and fluorescence activated cell sorting (FACS). A two-site, monoclonal-based immunoassay using monoclonal antibodies reactive to two non-interfering epitopes on an MRP5-like protein polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding MRP5-like protein polypeptides include oligolabeling, nick translation, end-labeling, or PCR amplification using a labeled nucleotide. Alternatively, sequences encoding an MRP5-like protein polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding an MRP5-like protein polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode MRP5-like protein polypeptides can be designed to contain signal sequences which direct secretion of soluble MRP5-like protein polypeptides through a prokaryotic or eukaryotic cell membrane or which direct the membrane insertion of membrane-bound MRP5-like protein polypeptide.

As discussed above, other constructions can be used to join a sequence encoding an. MRP5-like protein polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the MRP5-like protein polypeptide also can be used to facilitate purification. One such expression vector provides for expression of a fusion protein containing an MRP5-like protein polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif* 3, 263–281, 1992), while the enterokinase cleavage site provides a means for purifying the MRP5-like protein polypeptide from the fusion protein. Vectors that contain fusion proteins are disclosed in Kroll et al., *DNA Cell Biol.* 12, 441–453, 1993.

Chemical Synthesis

Sequences encoding an MRP5-like protein polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, an MRP5-like protein polypeptide itself can be produced using chemical methods to synthesize its amino acid sequence, such as by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of MRP5-like protein polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic MRP5-like protein polypeptide can be confirmed by amino acid analysis or sequencing (e.g., the Edman degradation procedure; see Creighton, supra). Additionally, any portion of the amino acid sequence of the MRP5-like protein polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce MRP5-like protein polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life that is longer than that of a transcript generated from the naturally occurring sequence.

The nucleotide sequences disclosed herein can be engineered using methods generally known in the art to alter MRP5-like protein polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of an MRP5-like protein polypeptide. "Antibody" as used herein includes intact immunoglobulin molecules, as well as fragments thereof, such as Fab, F(ab')$_2$, and Fv, which are capable of binding an epitope of an MRP5-like protein polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of an MRP5-like protein polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody that specifically binds to the immunogen.

Typically, an antibody which specifically binds to an MRP5-like protein polypeptide provides a detection signal at least 5-, 10-, or 20-fold higher than a detection signal provided with other proteins when used in an immunochemical assay. Preferably, antibodies which specifically bind to MRP5-like protein polypeptides do not detect other proteins in immunochemical assays and can immunoprecipitate an MRP5-like protein polypeptide from solution.

Human MRP5-like protein polypeptides can be used to immunize a mammal, such as a mouse, rat, rabbit, guinea pig, monkey, or human, to produce polyclonal antibodies. If desired, an MRP5-like protein polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g lysolecithin, pluronic polyols, polyanions, peptides, oil emulsions, keyhole limpet hemocyanin, and dinitrophenol). Among adjuvants used in humans, BCG (*bacilli Calmette-Guerin*) and *Corynebacterium parvum* are especially useful.

Monoclonal antibodies that specifically bind to an MRP5-like protein polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies that specifically bind to an MRP5-like protein polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies that specifically bind to MRP5-like protein polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to MRP5-like protein polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which an MRP5-like protein polypeptide is bound. The bound antibodies can then be eluted from the column using a buffer with a high salt concentration.

Antisense Oligonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of MRP5-like protein gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of MRP5-like protein gene expression can be obtained by designing antisense oligonucleotides that will form duplexes to the control, 5', or regulatory regions of the MRP5-like protein gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of an MRP5-like protein polynucleotide. Antisense oligonucleotides which comprise, for example, 2, 3, 4, or 5 or more stretches of contiguous nucleotides which are precisely complementary to an MRP5-like protein polynucleotide, each separated by a stretch of contiguous nucleotides which are not complementary to adjacent MRP5-like protein nucleotides, can provide sufficient targeting specificity for MRP5-like protein mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular MRP5-like protein polynucleotide sequence.

Antisense oligonucleotides can be modified without affecting their ability to hybridize to an MRP5-like protein polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide.

These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage.

Examples include engineered hammerhead motif ribozyme molecules that can specifically and efficiently catalyze endonucleolytic cleavage of specific nucleotide sequences.

The coding sequence of an MRP5-like protein polynucleotide can be used to generate ribozymes that will specifically bind to mRNA transcribed from the MRP5-like protein polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within an MRP5-like protein RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate MRP5-like protein RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease MRP5-like protein expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors that induce expression of a target gene. Ribozymes also can be engineered to provide an additional level of regulation, so that destruction of mRNA occurs only when both a ribozyme and a target gene are induced in the cells.

Differentially Expressed Genes

Described herein are methods for the identification of genes whose products interact with human MRP5-like protein. Such genes may represent genes that are differentially expressed in disorders including, but not limited to, cardiovascular disorders, cancer, and CNS disorders. Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human MRP5-like protein gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects.

Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., *Proc. Natl. Acad. Sci. U.S.A.* 85, 208–12, 1988), subtractive hybridization (Hedrick et al., *Nature* 308, 149–53; Lee et al., *Proc. Natl. Acad. Sci. U.S.A.* 88, 2825, 1984), and, preferably, differential display (Liang & Pardee, *Science* 257, 967–71, 1992; U.S. Pat. No. 5,262,311).

The differential expression information may itself suggest relevant methods for the treatment of disorders involving the human MRP5-like protein. For example, treatment may include a modulation of expression of the differentially expressed genes and/or the gene encoding the human MRP5-like protein. The differential expression information may indicate whether the expression or activity of the differentially expressed gene or gene product or the human MRP5-like protein gene or gene product are up-regulated or down-regulated.

Screening Methods

The invention provides assays for screening test compounds that bind to or modulate the activity of an MRP5-like protein polypeptide or an MRP5-like protein polynucleotide.

A test compound preferably binds to an MRP5-like protein polypeptide or polynucleotide. More preferably, a test compound decreases or increases a biological activity of the protein by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad. Sci.* 97, 6378–6382, 1990; Felici, *J. Mol. Biol.* 222, 301–310, 1991; and Ladner, U.S. Pat. No. 5,223,409).

High Throughput Screening

Test compounds can be screened for the ability to bind to MRP5-like protein polypeptides or polynucleotides or to affect MRP5-like protein activity or MRP5-like protein gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In thus method, test samples are placed in a porous matrix. One or more assay components are then placed within, on top of, or at the bottom of a matrix such as a gel, a plastic sheet, a filter, or other form of easily manipulated solid support.

When samples are introduced to the porous matrix they diffuse sufficiently slowly, such that the assays can be performed without the test samples running together.

Binding Assays

For binding assays, the test compound is preferably a small molecule that binds to a MRP5-like protein polypeptide, such that normal biological activity is prevented. Examples of such small molecules include, but are not limited to, small peptides or peptide-like molecules.

In binding assays, either the test compound or the MRP5-like protein polypeptide can comprise a detectable label, such as a fluorescent, radioisotopic, chemiluminescent, or enzymatic label, such as horseradish peroxidase, alkaline phosphatase, or luciferase. Detection of a test compound that is bound to the MRP5-like protein polypeptide can then be accomplished, for example, by direct counting of radio-emmission, by scintillation counting, or by determining conversion of an appropriate substrate to a detectable product.

Alternatively, binding of a test compound to an MRP5-like protein polypeptide can be determined without labeling either of the interactants. For example, a microphysiometer can be used to detect binding of a test compound with an MRP5-like protein polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and an MRP5-like protein polypeptide (McConnell et al., *Science* 257, 1906–1912, 1992).

Determining the ability of a test compound to bind to an MRP5-like protein polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, an MRP5-like protein polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the MRP5-like protein polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding an MRP5-like protein polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor.

NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to an MRP5-like protein polypeptide, polynucleotide, or a test compound, but which do not interfere with a desired binding site can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the MRP5-like protein polypeptide or test compound, enzyme-linked assays which rely on detecting an activity of the MRP5-like protein polypeptide, and SDS gel electrophoresis under non-reducing conditions.

Screening for test compounds which bind to an MRP5-like protein polypeptide or polylnucleotide also can be carried out in an intact cell. Any cell which comprises an MRP5-like protein polypeptide or polynucleotide can be used in a cell-based assay system. AN MRP5-like protein polynucleotide can be naturally occurring in the cell or can be introduced using techniques such as those described above. Binding of the test compound to an MRP5-like protein polypeptide or polynucleotide is determined as described above.

Gene Expression

In another embodiment, test compounds that increase or decrease MRP5-like protein gene expression are identified. An MRP5-like protein polynucleotide is contacted with a test compound, and the expression of an RNA or polypeptide product of the MRP5-like protein polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of MRP5-like protein mRNA or polypeptide expression in the cells can be determined by methods well known in the art for detecting mRNA or polypeptide. Either qualitative or quantitative methods can be used. The presence of polypeptide products of an MRP5-like protein polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into an MRP5-like protein polypeptide.

Such screening can be carried out either in a cell-free assay system or in an intact cell. Any cell that expresses an MRP5-like protein polynucleotide can be used in a cell-based assay system. The MRP5-like protein polynucleotide can be naturally occurring in the cell or can be introduced using techniques such as those described above. Either a primary culture or an established cell line, such as CHO or human embryonic kidney 293 cells, can be used.

Assays for Biological Activity

Test compounds can be screened for the ability to regulate the ability of MRP5-like protein to transport various compounds. For example, transport of therapeutic agents can be assessed, e.g., as described in Wijnholds et al., *Proc. Natl. Acad. Sci. U.S.A.* 97, 7476–81, 2000. Transport of cGMP can be assessed, e.g., as described in Jedlitchsky et al., *J. Biol. Chem.* 275, 30069–74, 2000. Such assays can be carried out, for example, after contacting an intact cell with a test compound. A test compound that decreases transport activity of an MRP5-like protein polypeptide by at least about 10, preferably about 50, more preferably about 75, 90, or 100% is identified as a potential therapeutic agent for decreasing MRP5-like protein activity. A test compound which increases transport activity of a human MRP5-like protein polypeptide by at least about 10, preferably about 50, more preferably about 75, 90, or 100% is identified as a potential therapeutic agent for increasing human MRP5-like protein activity.

Pharmaceutical Compositions

The invention also provides pharmaceutical compositions that can be administered to a patient to achieve a therapeutic effect. Pharmaceutical compositions of the invention can comprise, for example, an MRP5-like protein polypeptide, MRP5-like protein polynucleotide, ribozymes or antisense oligonucleotides, antibodies which specifically bind to an MRP5-like protein polypeptide, or mimetics, activators, or inhibitors of an MRP5-like protein polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

ATP-binding cassette (ABC) transporters, play a critical role in cellular detoxification processes. These transporters provide an innate, but in many respects also adaptive, defense system against toxins, harmful metabolic compounds, and inherently toxic therapeutic agents. Hydrophobic, toxic substances readily penetrate the membrane system of the cell. Importantly, a subset of the ABC transporter mediates the export of a wide variety of such substances. Besides their classical function as multidrug resistance (MRP) genes, MRP1 and MRP3 are capable of translocating phospholipids between the internal and external plasma membrane leaflet. Recent studies in the human CaCo cell line suggest a role for MRP1 in the translocation of cholesterol from the plasma membrane to the endoplasmic reticulum. The emerging concept that members of the ABC transporter family are critically involved in cellular lipid trafficking has been convincingly substantiated by the recent discovery of additional ABC family members for which key regulatory functions in physiologic lipid transport processes could be demonstrated. The group of these ABC transporters include MRP5 and BSEP, which was shown to play a crucial role in hepatic excretion of bile salts and glutathione conjugates into the bile. Furthermore, the disruption of MRP2 in mouse mutants resulted in the virtual absence of ATP-dependent biliary phospholipid and cholesterol secretion, leading to a marked reduction of serum HDL cholesterol and VLDL triglycerides. These abnormalities in lipid metabolism may be caused by a reduced MRP2-dependent absorption of dietary and biliary lipids.

Human MRP5-like protein can be regulated to treat cardiovascular disorders, cancer, and CNS disorders. ABC transporters are involved in cellular detoxification processes, protecting cells against toxins, harmful metabolic compounds, and toxic therapeutic agents. Recent studies suggest that multidrug resistance proteins (MRPs), may be involved in translocating phospholipids and cholesterol across the cellular membrane. ABC transporters play a role in lipid transport and inflammation, which may contribute to arteriosclerosis. One human ABC transporter, MRP5, when stably expressed in V79 hamster lung fibroblasts, transports cyclic nucleotides such as cGMP. Jedlitschky et al., 2000. This transport was inhibited by phosphodiesterase inhibitors such as Sildenafil, Trequinsin, and Zaprinast. Id. Cyclic GMP plays a major role in signal transduction pathways, including smooth muscle relaxation, neural communication, and platelet aggregation.

The affinity of MRP5 for cGMP suggests MRP5 as a potential pharmacological target for cardiovascular conditions such as arterial hypertension, cardiac arrhythmias, and angina pectoris. Cardiovascular diseases include the following disorders of the heart and the vascular system: congestive heart failure, myocardial infarction, ischernic diseases of the heart, all kinds of atrial and ventricular arrhythmias, hypertensive vascular diseases, and peripheral vascular diseases.

Heart failure is defined as a pathophysiologic state in which an abnormality of cardiac function is responsible for the failure of the heart to pump blood at a rate commensurate with the requirement of the metabolizing tissue. It includes all forms of pumping failure, such as high-output and low-output, acute and chronic, right-sided or left-sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included, as well as the acute treatment of MI and the prevention of complications.

Ischemic diseases are conditions in which the coronary flow is restricted resulting in a perfusion which is inadequate to meet the myocardial requirement for oxygen. This group of diseases includes stable angina, unstable angina, and asymptomatic ischemia.

Arrhythmias include all forms of atrial and ventricular tachyarrhythmias (atrial tachycardia, atrial flutter, atrial fibrillation, atrio-ventricular reentrant tachycardia, preexcitation syndrome, ventricular tachycardia, ventricular flutter, and ventricular fibrillation), as well as bradycardic forms of arrhythmias.

Vascular diseases include primary as well as all kinds of secondary arterial hypertension (renal, endocrine, neurogenic, others). The disclosed gene and its product may be used as drug targets for the treatment of hypertension as well as for the prevention of all complications. Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon, and venous disorders.

MRPs also play a defensive role for cancer cells against chemotherapeutic agents and virally infected cells against anti-viral agents. MRPs act as multispecific organic anion pumps including nucleotide analogs. In polarized Madin-Darby canine kidney II cells which overexpress human MRP5, MRP5 mediates transport of S-(2,4-dinitrophenyl) glutathione and glutathione; these cells are resistant to the thiopurine anticancer drugs 6-mercaptopurine (6-MP) and thioguanine. Wijnholds et al., 2000. The transfected cells also transport of the anti-HIV drug 9-(2-phosphonyl-methoxyethyl)-adenine (PMEA). Id. This transport is inhibited by inhibitors of organic anion transport. Id. Selective inhibition of MRPs may enhance the therapeutic efficacy of anticancer and antiviral drugs, by decreasing the export of therapeutic agents and thus increasing their intracellular concentration and efficacy.

Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Activators and/or inhibitors of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

Central and peripheral nervous system disorders also can be treated, such as primary and secondary disorders after brain injury, disorders of mood, anxiety disorders, disorders of thought and volition, disorders of sleep and wakefulness, diseases of the motor unit, such as neurogenic and myopathic disorders, neurodegenerative disorders such as Alzheimer's and Parlinson's disease, and processes of peripheral and chronic pain.

Pain that is associated with CNS disorders also can be treated by regulating the activity of human MRP5-like protein. Pain which can be treated includes that associated with central nervous system disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with cancer and cancer treatment also can be treated, as can headache pain (for example, migraine with aura, migraine without aura, and other migraine disorders), episodic and chronic tension-type headache, tension-type like headache, cluster headache, and chronic paroxysmal hemicrania.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or an MRP5-like protein polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects MRP5-like protein activity can be administered to a human cell, either in vitro or in vivo, to reduce MRP5-like protein activity. The reagent preferably binds to an expression product of a human MRP5-like protein gene. If the expression product is a protein, the reagent is preferably an antibody. For treatment of human cells ex vivo, an antibody can be added to a preparation of stem cells that have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart, brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $10^6$ cells, more preferably about 1.0 µg of DNA per 16 nmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Senko et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is well within the capability of those skilled in the art. A therapeutically effective dose refers to that amount of active ingredient which increases or decreases MRP5-like protein activity relative to the MRP5-like protein activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides that express antisense oligonucleotides or ribozymes can be introduced into cells by a variety of methods, as described above.

Preferably, a reagent reduces expression of an MRP5-like protein gene or the activity of an MRP5-like protein polypeptide by at least about 10, preferably about 50, more preferably about 75, 90, or 100% relative to the absence of the reagent. The effectiveness of the mechanism chosen to decrease the level of expression of an MRP5-like protein gene or the activity of an MRP5-like protein polypeptide can be assessed using methods well known in the art, such as hybridization of nucleotide probes to MRP5-like protein-specific mRNA, quantitative RT-PCR, immunologic detection of an MRP5-like protein polypeptide, or measurement of MRP5-like protein activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human MRP5-like protein also can be used in diagnostic assays for detecting diseases and abnormalities or susceptibility to diseases and abnormalities related to the presence of mutations in the nucleic acid sequences that encode the polypeptide. For example, differences can be determined between the cDNA or genomic sequence encoding MRP5-like protein in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and S 1 protection or the chemical cleavage method (e.g., Cotton et al., *Proc. Natl. Acad. Sci. USA* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of MRP5-like protein also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

Detection of MRP5-Like Protein Activity

The polynucleotide of SEQ ID NO: 1 is inserted into the expression vector pCEV4 and the expression vector pCEV4-MRP5-like protein polypeptide obtained is transfected into human embryonic kidney 293 cells. These cells are incubated for 24 h at 37° C. under 5% CO2/95% air. Dilution series of 6-mercaptopurine (6-MP), in 100 µl of conditioned medium are added to the cells and incubated for 5 days at 37° C. Medium is removed and cells are frozen at −80° C. Cells are thawed and the total number of cells is determined fluorimetrically by using the CyQuant Cell Proliferation Assay Kit Molecular Probes) and the CytoFluor 4000 fluorescence plate reader (PerSeptive Biosystems, Framingham, Mass.). The relative resistance is calculated as the ratio of 50% inhibition of growth (IC50) of the resistant cell line to the IC 50 of the parental cell line. It is shown that the polypeptide of SEQ ID NO: 2 has a MRP5-like protein activity.

EXAMPLE 2

Expression of Recombinant Human MRP5-Like Protein

The *Pichia pastoris* expression vector pPICZB (Invitrogen, San Diego, Calif.) is used to produce large quantities of recombinant human MRP5-like protein polypeptides in yeast. The MRP5-like protein-encoding DNA sequence is derived from SEQ ID NO: 1. Before insertion into vector pPICZB, the DNA sequence is modified by well known methods in such a way that it contains at its 5'-end an initiation codon and at its 3'-end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human MRP5-like protein polypeptide is obtained.

EXAMPLE 3

Identification of Test Compounds that Bind to MRP5-Like Protein Polypeptides

Purified MRP5-like protein polypeptides comprising a glutathione-S-transferase protein and absorbed onto glutathione-derivatized wells of 96-well microtiter plates are contacted with test compounds from a small molecule library at pH 7.0 in a physiological buffer solution. Human MRP5-like protein polypeptides comprise the amino acid sequence shown in SEQ ID NO: 2. The test compounds comprise a fluorescent tag. The samples are incubated for 5 minutes to one hour. Control samples are incubated in the absence of a test compound.

The buffer solution containing the test compounds is washed from the wells. Binding of a test compound to an MRP5-like protein polypeptide is detected by fluorescence measurements of the contents of the wells. A test compound that increases the fluorescence in a well by at least 15% relative to fluorescence of a well in which a test compound is not incubated is identified as a compound which binds to an MRP5-like protein polypeptide.

EXAMPLE 4

Identification of a Test Compound which Decreases MRP5-like Protein Gene Expression A test compound is administered to a culture of human cells transfected with an MRP5-like protein expression construct and incubated at 37° C. for 10 to 45 minutes. A culture of the same type of cells that have not been transfected is incubated for the same time without the test compound to provide a negative control.

RNA is isolated from the two cultures as described in Chirgwin et al., *Biochem.* 18, 5294–99, 1979). Northern blots are prepared using 20 to 30 µg total RNA and hybridized with a $^{32}$P-labeled MRP5-like protein-specific probe at 65° C. in Express-hyb (CLONTECH). The probe comprises at least 11 contiguous nucleotides selected from the complement of SEQ ID NO: 1. A test compound that decreases the MRP5-like protein-specific signal relative to the signal obtained in the absence of the test compound is identified as an inhibitor of MRP5-like protein gene expression.

EXAMPLE 5

Identification of a Test Compound which Inhibits MMP5-like Protein Activity

A test compound is administered to a culture of human cells transfected with a MMP5-like protein expression construct and incubated at 37° C. for 10 to 45 minutes. A culture of the same type of cells that have not been transfected is incubated for the same time without the test compound to provide a negative control. Transport of therapeutic agents in the presence and absence of the test compound is assessed as described in Wijnholds et al., *Proc. Natl. Acad. Sci. U.S.* 97, 7476–81, 2000. Transport of cGMP in the presence and absence of the test compound is assessed as described in Jedlitchsky et al., *J. Biol. Chem.* 275, 30069–74, 2000.

A test compound which decreases the transport of a therapeutic agent or of cGMP relative to such transport in the absence of the test compound is identified as an inhibitor of MMP5-like protein activity.

EXAMPLE 6

Tissue-specific Expression of MRP5-like Protein

The qualitative expression pattern of MRP5-like protein in various tissues is determined by Reverse Transcription-Polymerase Chain Reaction (RT-PCR). To demonstrate that MRP5-like protein is involved in cancer, expression is determined in the following tissues: adrenal gland, bone marrow, brain, cerebellum, colon, fetal brain, fetal liver, heart, kidney, liver, lung, mammary gland, pancreas, placenta, prostate, salivary gland, skeletal muscle, small intestine, spinal cord, spleen, stomach, testis, thymus, thyroid, trachea, uterus, and peripheral blood lymphocytes. Expression in the following cancer cell lines also is determined: DU-145 (prostate), NCI-H125 (lung), HT-29 (colon), COLO-205 (colon), A-549 (lung), NCI-H460 (lung), HT-116 (colon), DLD-1 (colon), MDA-MD-231 (breast), LS174T (colon), ZF-75 (breast), MDA-MN-435 (breast), HT-1080, MCF-7 (breast), and U87. Matched pairs of malignant and normal tissue from the same patient also are tested.

To demonstrate that MRP5-like protein is involved in CNS disorders, the following tissues are screened: fetal and adult brain, muscle, heart, lung, kidney, liver, thymus, testis, colon, placenta, trachea, pancreas, kidney, gastric mucosa, colon, liver, cerebellum, skin, cortex (Alzheimer's and normal), hypothalamus, cortex, amygdala, cerebellum, hippocampus, choroid, plexus, thalamus, and spinal cord.

Quantitative expression profiling. Quantitative expression profiling is performed by the form of quantitative PCR analysis called "kinetic analysis" firstly described in Higuchi et al., *BioTechnology* 10, 413–17, 1992, and Higuchi et al., *BioTechnology* 11, 1026–30, 1993. The principle is that at any given cycle within the exponential phase of PCR, the amount of product is proportional to the initial number of template copies.

If the amplification is performed in the presence of an internally quenched fluorescent oligonucleotide (TaqMan probe) complementary to the target sequence, the probe is cleaved by the 5'-3' endonuclease activity of Taq DNA polymerase and a fluorescent dye released in the medium (Holland et al., *Proc. Natl. Acad. Sci. U.S.A.* 88, 7276–80, 1991). Because the fluorescence emission will increase in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

The amplification of an endogenous control can be performed to standardize the amount of sample RNA added to a reaction. In this kind of experiment, the control of choice is the 18S ribosomal RNA. Because reporter dyes with differing emission spectra are available, the target and the endogenous control can be independently quantified in the same tube if probes labeled with different dyes are used.

All "real time PCR" measurements of fluorescence are made in the ABI Prism 7700.

RNA extraction and cDNA preparation. Total RNA from the tissues listed above are used for expression quantification. RNAs labeled "from autopsy" were extracted from autoptic tissues with the TRIzol reagent (Life Technologies, MD) according to the manufacturer's protocol.

Fifty μg of each RNA were treated with DNase I for 1 hour at 37° C. in the following reaction mix: 0.2 U/μl RNase-free DNase I (Roche Diagnostics, Germany); 0.4 U/μl RNase inhibitor (PE Applied Biosystems, CA); 10 mM Tris-HCl pH 7.9; 10 mM $MgCl_2$; 50 mM NaCl; and 1 mM DTT.

After incubation, RNA is extracted once with I volume of phenol:chloroform:isoamyl alcohol (24:24:1) and once with chloroform, and precipitated with 1/10 volume of 3 M NaAcetate, pH5.2, and 2 volumes of ethanol.

Fifty μg of each RNA from the autoptic tissues are DNase treated with the DNA-free kit purchased from Ambion (Ambion, Tex.). After resuspension and spectrophotometric quantification, each sample is reverse transcribed with the TaqMan Reverse Transcription Reagents (PE Applied Biosystems, CA) according to the manufacturer's protocol. The final concentration of RNA in the reaction mix is 200 ng/μL. Reverse transcription is carried out with 2.5 μM of random hexamer primers.

TaqMan quantitative analysis. Specific primers and probe are designed according to the recommendations of PE Applied Biosystems; the probe can be labeled at the 5' end FAM (6-carboxy-fluorescein) and at the 3' end with TAMRA (6-carboxy-tetramethyl-rhodamine).

Quantification experiments are performed on 10 ng of reverse transcribed RNA from each sample. Each determination is done in triplicate. Total cDNA content is normalized with the simultaneous quantification (multiplex PCR) of the 18S ribosomal RNA using the Pre-Developed TaqMan Assay Reagents (PDAR) Control Kit (PE Applied Biosystems, CA).

The assay reaction mix is as follows: 1×final TaqMan Universal PCR Master Mix (from 2× stock) (PE Applied Biosystems, CA); 1×PDAR control-18S RNA (from 20× stock); 300 nM forward primer; 900 nM reverse primer; 200 nM probe; 10 ng cDNA; and water to 25 μl.

Each of the following steps are carried out once: pre PCR, 2 minutes at 50° C., and 10 minutes at 95° C. The following steps are carried out 40 times: denaturation, 15 seconds at 95° C., annealing/extension, 1 minute at 60° C.

The experiment is performed on an ABI Prism 7700 Sequence Detector (PE Applied Biosystems, CA). At the end of the run, fluorescence data acquired during PCR are processed as described in the ABI Prism 7700 user's manual in order to achieve better background subtraction as well as signal linearity with the starting target quantity.

EXAMPLE 7

Expression Profiling

Total cellular RNA was isolated from cells by one of two standard methods: (1) guanidine isothiocyanate/Cesium chloride density gradient centrifugation or (2) the Tri-Reagent protocol according to the manufacturer's specifications (Molecular Research Center, Inc., Cincinnati, Ohio). Total RNA prepared by the Tri-reagent protocol was treated with DNase I to remove genomic DNA contamination. RNA was prepared from coronary smooth muscle cells, brain, testis, pancreas, stomach, cerebellum, trachea, adrenal gland, skeletal muscle, salivary gland, small intestine, prostate, fetal liver, placenta, fetal brain, uterus, mammary gland, heart, spleen, lung, HeLa cells, liver, kidney, thymus, bone marrow, thyroid, colon, bladder, spinal cord, peripheral blood, liver cirrhosis, pancreas liver cirrhosis, spleen liver cirrhosis, total Alzheimer brain, fetal lung, breast tumor, colon tumor, lung tumor, HEK 293 cells, adipose, pericardium, fetal heart, thyroid tumor, MDA MB 231 cells, HEP G2 cells, HUVEC cells, fetal kidney, breast, Jurkat T-cells, Alzheimer brain cortex, cervix, esophagus, thalamus, precentral gyrus, hippocampus, occipital lobe, cerebral peduncles, postcentral gyrus, temporal lobe, parietal lobe, cerebellum (right), cerebellum (left), tonsilla cerebelli, cerebral meninges, pons, frontal lobe, cerebral cortex, corpus callosum, vermis cerebelli, Alzheimer brain frontal lobe, interventricular septum, heart atrium (right), heart atrium (left), and heart ventricle (left).

For relative quantitation of the mRNA distribution of MRP5-like protein, total RNA from each cell or tissue source was first reverse transcribed. Eighty-five μg of total RNA was reverse transcribed using 1 μmole random hexamer primers, 0.5 mM each of DATP, dCTP, dGTP, and dTTP (Qiagen, Hilden, Germany), 3000 U RnaseQut (Invitrogen, Groningen, Netherlands) in a final volume of 680 μl. The first strand synthesis buffer and Omniscript (2 U/μl) reverse transcriptase were from (Qiagen, Hilden, Germany). The reaction was incubated at 37° C. for 90 minutes and cooled on ice. The volume was adjusted to 6800 μl with water, yielding a final concentration of 12.5 ng/μl of starting RNA. For relative quantitation of the distribution of MRP5-like protein mRNA in cells and tissues the Perkin Elmer ABI Prism®. 7700 Sequence Detection system or Biorad iCycler was used according to the manufacturer's specifications and protocols. PCR reactions were set up to quantitate MRP5-like protein and the housekeeping genes HPRT, GAPDH, beta-actin, and others. Forward and reverse primers and probe were designed using the Perkin Elmer ABI Primer Express™ software and were synthesized by TibMolBiol (Berlin, Germany). The MRP5-like protein forward primer sequence was: GCAGCTGGCGTCCAGCT (SEQ ID NO: 7). The MRP5-like protein reverse primer sequence was TGCAGTATCCTCTCTACAGCCG (SEQ ID NO: 8). The fluorogenic probe, labeled with FAM as the reporter dye and TAMRA as the quencher, is CACTGCCCGGATTGGCT-TGGA (SEQ ID NO: 9).

The following reactions in a final volume of 25 μl were set up: 1×TaqMan buffer A, 5.5 mM MgCl2, 200 nM each of dATP, dCTP, dGTP, and dUTP, 0.025 U/μl AmpliTaq Gold™, 0.01 U/μl AmpErase UNG® and probe 1×, MRP5-like protein forward and, reverse primers each at 200 nM, 200 nM MRP5-like protein FAM/TAMRA-labeled probe, and 5 μl of template cDNA. Thermal cycling parameters were 2 min HOLD at 50° C., 10 min HOLD at 95° C., followed by melting at 95° C. for 15 sec and annealing/extending at 60° C. for 1 min for each of 40 cycles.

Calculation of Corrected CT Values

The CT-value is calculated as described above. The CF-value is calculated as followed:

1. PCR reactions were set up to quantitate the housekeeping genes (HKG) for each cDNA sample.
2. $CT_{HKG}$-values were calculated as described above
3. CT-mean values of all HKG for each cDNA are calculated (n=number of HKG):

$(CT_{HKG1}\text{-value}+CT_{HKG2}\text{-value}+CT_{HKG-X}\text{-value})/$
  $n=CT_{cDNA-X}\text{-mean values (n=number of HKG)}$ 4. $(CT_{cDNA-1}\text{-mean value}+CT_{cDNA-X}\text{-mean value})/$
   $y=CT_{pannel}\text{-mean value (y=number of cDNAs)}$ 5. $CT_{pannel}\text{-mean value} - CT_{cDNA-X}\text{-mean value}=CF_{cDNA-X}$ 6. $CT_{cDNA-x}+CF_{cDNA-X}=CT_{cor-cDNA-X}$ Calculation of Relative Expression Definition: highest $CT_{cor-cDNA-X}\neq 40$ is defined as $CT_{cor-cDNA-X}$ [high]

Relative Expression=$2e(CT_{cor-cDNA-X}\text{[high]}-CT_{cor-cDNA-Y})$

Figure 12:
FIG. 12 shows the Expression profiling of MRP5-like protein
Figure 13:
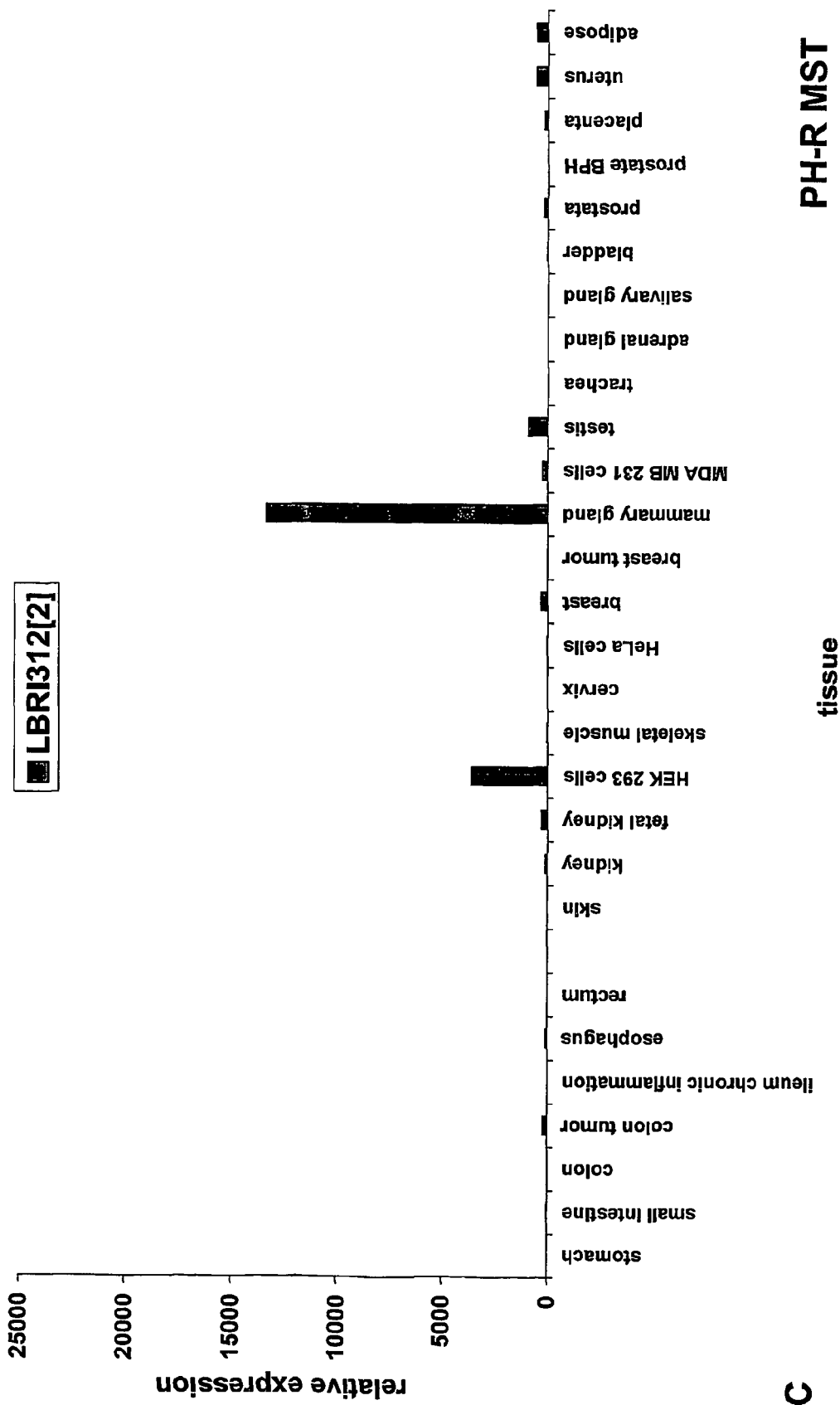
FIG. 13 shows the Expression profiling of MRP5-like protein

The results of the mRNA-quantification (expression profiling) are shown in FIGS. 11–13.

MRP5-like protein is expressed in different human tissues. The receptor is highly expressed in total Alzheimer brain, Alzheimer brain cortex, cerebral peduncles, postcentral gyrus, cerebral meninges, thyroid tumor, liver, liver (cirrhosis), HEK293 cells, mammary gland. The receptor is highly expressed in different brain tissues as total Alzheimer brain, Alzheimer brain cortex, cerebral peduncles, postcentral gyrus and cerebral meninges. The expression in the above mentioned tissues suggests an association between MRP5-like protein and peripheral and central nervous system diseases.

The receptor is highly expressed in thyroid tumor. The expression in the above mentioned tissues suggests an association between MRP5-like protein and cancer.

The receptor is highly expressed in liver, liver (cirrhosis), HEK293. The expression in the above mentioned tissues suggests an association between MRP5-like protein and diseases of the liver and kidney.

The receptor is highly expressed in mammary gland. The expression in the above mentioned tissues suggests an association between MRP5-like protein and diseases of secretory organs.

REFERENCES

1. ABC transporters in lipid transport, Borst P, Zelcer N, van Helvoort A, Biochim Biophys Acta 2000 Jun. 26;1486(1)
2. ABC1: the gene for Tangier disease and beyond, Ordovas J M, Nutr Rev 2000 March;58(3 Pt 1):76–9
3. Multidrug resistance, Schneider E, Paul D, Ivy P, Cowan K H, Cancer Chemother Biol Response Modif 1999;18: 152–77
4. The multidrug resistance protein 5 functions as an ATP-dependent export pump for cyclic nucleotides, Jedlitschky G, Burchell B, Keppler D, J Biol Chem. 2000 Sep. 29;275(39):30069–74.
5. Multidrug-resistance protein 5 is a multispecific organic anion transporter able to transport nucleotide analogs, Wijnholds J, Mol C A, van Deemter L, de Haas M, Scheffer G L, Baas F, Beijnen J H, Scheper R J, Hatse S, De Clercq E, Balzarini J, Borst P, Proc Natl Acad Sci USA. 2000 Jun. 20;97(13):7476–81.

The invention claimed is:

1. An isolated and purified protein comprising a first polypeptide segment comprising the amino acid sequence shown in SEQ ID NO:2.

2. The protein of claim 1 further comprising a second polypeptide segment comprising an amino acid sequence which is not the amino acid sequence of SEQ ID NO:2, wherein the second polypeptide segment is joined to the first polypeptide segment by means of a peptide bond.

3. An isolated and purified protein comprising an amino acid sequence which is at least 99% identical to the amino acid sequence shown in SEQ ID NO:2 and which has an ATPase activity.

4. An isolated and purified polynucleotide which encodes the amino acid sequence shown in SEQ ID NO:2.

5. The polynucleotide of claim 4 which comprises the nucleotide sequence shown in SEQ ID NO:1.

6. The polynucleotide of claim 4 which is a cDNA.

7. An isolated and purified single stranded polynucleotide comprising SEQ ID NO:1 or a complement of said sequence, wherein the protein comprises the amino acid sequence shown in SEQ ID NO:2 and the coding sequence comprises SEQ ID NO:1.

8. An expression construct, comprising;
a coding sequence for the amino acid sequence shown in SEQ ID NO:2; and
a promoter which is located upstream from the coding sequence and which controls expression of the coding sequence.

9. The expression construct of claim 8 wherein the coding sequence comprises the nucleotide sequence of SEQ ID NO:1.

10. A host cell comprising an expression construct, wherein the expression construct comprises:
a coding sequence for a protein comprising the amino acid sequence shown in SEQ ID NO:2; and
a promoter which is located upstream from the coding sequence and which controls expression of the coding sequence.

11. The host cell of claim 10 which is prokaryotic.

12. The host cell of claim 10 which is eukaryotic.

13. A method of producing a protein, comprising the steps of:
culturing a host cell in a culture medium, wherein the host cell comprises an expression construct comprising (a) a coding sequence for a protein comprising the amino acid sequence shown in SEQ ID NO:2 and (b) a promoter which is located upstream from the coding sequence and which controls expression of the coding sequence, wherein the step of culturing is carried out under conditions whereby the protein is expressed; and
recovering the protein.

14. A composition comprising:
a protein comprising the amino acid sequence shown in SEQ ID NO:2; and
a pharmaceutically acceptable carrier.

15. A composition comprising:
a polynucleotide encoding a protein comprising the amino acid sequence shown in SEQ ID NO:2; and
a pharmaceutically acceptable carrier.

16. The composition of claim 15 wherein the polynucleotide comprises the nucleotide sequence shown in SEQ ID NO:1.

* * * * *

SEQUENCE LISTING

<160> NUMBER OF SEQ ID NOS: 10

<210> SEQ ID NO 1
<211> LENGTH: 4035
<212> TYPE: DNA
<213> ORGANISM: Homo sapiens
<220> FEATURE:
<221> NAME/KEY: CDS
<222> LOCATION: (1)..(4035)
<223> OTHER INFORMATION:

<400> SEQUENCE: 1

```
atg act agg aag agg aca tac tgg gtg ccc aac tct tct ggt ggc ctc        48
Met Thr Arg Lys Arg Thr Tyr Trp Val Pro Asn Ser Ser Gly Gly Leu
1               5                   10                  15 gtg aat cgt ggc atc gac ata ggc gat gac atg gtt tca gga ctt att        96
Val Asn Arg Gly Ile Asp Ile Gly Asp Asp Met Val Ser Gly Leu Ile
            20                  25                  30 tat ccc ctg gac aat gct ggc ctg ttc tcc tac ctc acc gtg tca tgg       144
Tyr Pro Leu Asp Asn Ala Gly Leu Phe Ser Tyr Leu Thr Val Ser Trp
        35                  40                  45 ctc acc ccg ctc atg atc caa agc tta cgg agt cgc tta gat gag aac       192
Leu Thr Pro Leu Met Ile Gln Ser Leu Arg Ser Arg Leu Asp Glu Asn
    50                  55                  60 acc atc cct cca ctg tca gtc cat gat gcc tca gac aaa aat gtc caa       240
Thr Ile Pro Pro Leu Ser Val His Asp Ala Ser Asp Lys Asn Val Gln
65                  70                  75                  80 agg ctt cac cgc ctt tgg gaa gaa gaa gtc tca agg cga ggg att gaa       288
Arg Leu His Arg Leu Trp Glu Glu Glu Val Ser Arg Arg Gly Ile Glu
                85                  90                  95 aaa gct tca gtg ctt ctg gtg atg ctg agg ttc cag aga aca agg ttg       336
Lys Ala Ser Val Leu Leu Val Met Leu Arg Phe Gln Arg Thr Arg Leu
            100                 105                 110
```

```
att ttc gat gca ctt ctg ggc atc tgc ttc tgc att gcc agt gta ctc      384
Ile Phe Asp Ala Leu Leu Gly Ile Cys Phe Cys Ile Ala Ser Val Leu
            115                 120                 125 ggg cca ata ttg att ata cca aag atc ctg gaa tat tca gaa gag cag      432
Gly Pro Ile Leu Ile Ile Pro Lys Ile Leu Glu Tyr Ser Glu Glu Gln
130                 135                 140 ttg ggg aat gtt gtc cat gga gtg gga ctc tgc ttt gcc ctt ttt ctc      480
Leu Gly Asn Val Val His Gly Val Gly Leu Cys Phe Ala Leu Phe Leu
145                 150                 155                 160 tcc gaa tgt gtg aag tct ctg agt ttc tcc tcc agt tgg atc atc aac      528
Ser Glu Cys Val Lys Ser Leu Ser Phe Ser Ser Ser Trp Ile Ile Asn
                165                 170                 175 caa cgc aca gcc atc agg ttc cga gca gct gtt tcc tcc ttt gcc ttt      576
Gln Arg Thr Ala Ile Arg Phe Arg Ala Ala Val Ser Ser Phe Ala Phe
            180                 185                 190 gag aag ctc atc caa ttt aag tct gta ata cac atc acc tca gga gag      624
Glu Lys Leu Ile Gln Phe Lys Ser Val Ile His Ile Thr Ser Gly Glu
195                 200                 205 gcc atc agc ttc ttc acc ggt gat gta aac tac ctg ttt gaa ggg gtg      672
Ala Ile Ser Phe Phe Thr Gly Asp Val Asn Tyr Leu Phe Glu Gly Val
210                 215                 220 tgc tat gga ccc cta gta ctg atc acc tgc gca tcg ctg gtc atc tgc      720
Cys Tyr Gly Pro Leu Val Leu Ile Thr Cys Ala Ser Leu Val Ile Cys
225                 230                 235                 240 agc att tct tcc tac ttc att att gga tac act gca ttt att gcc atc      768
Ser Ile Ser Ser Tyr Phe Ile Ile Gly Tyr Thr Ala Phe Ile Ala Ile
                245                 250                 255 tta tgc tat ctc ctg gtt ttc cca ctg gcg gta ttc atg aca aga atg      816
Leu Cys Tyr Leu Leu Val Phe Pro Leu Ala Val Phe Met Thr Arg Met
            260                 265                 270 gct gtg aag gct cag cat cac aca tct gag gtc agc gac cag cgc atc      864
Ala Val Lys Ala Gln His His Thr Ser Glu Val Ser Asp Gln Arg Ile
275                 280                 285 cgt gtg acc agt gaa gtt ctc act tgc att aag ctg att aaa atg tac      912
Arg Val Thr Ser Glu Val Leu Thr Cys Ile Lys Leu Ile Lys Met Tyr
290                 295                 300 aca tgg gag aaa cca ttt gca aaa atc att gaa gac cta aga agg aag      960
Thr Trp Glu Lys Pro Phe Ala Lys Ile Ile Glu Asp Leu Arg Arg Lys
305                 310                 315                 320 gaa agg aaa cta ttg gag aag tgc ggg ctt gtc cag agc ctg aca agt     1008
Glu Arg Lys Leu Leu Glu Lys Cys Gly Leu Val Gln Ser Leu Thr Ser
                325                 330                 335 ata acc ttg ttc atc atc ccc aca gtg gcc aca gcg tcg tgg gtt ctc     1056
Ile Thr Leu Phe Ile Ile Pro Thr Val Ala Thr Ala Val Trp Val Leu
            340                 345                 350 atc cac aca tcc tta aag ctg aaa ctc aca gcg tca atg gcc ttc agc     1104
Ile His Thr Ser Leu Lys Leu Lys Leu Thr Ala Ser Met Ala Phe Ser
355                 360                 365 atg ctg gcc tcc ttg aat ctc ctt cgg ctg tca gtg ttc ttt gtg cct     1152
Met Leu Ala Ser Leu Asn Leu Leu Arg Leu Ser Val Phe Phe Val Pro
370                 375                 380 att gca gtc aaa ggt ctc acg aat tcc aag tct gca gtg atg agg ttc     1200
Ile Ala Val Lys Gly Leu Thr Asn Ser Lys Ser Ala Val Met Arg Phe
385                 390                 395                 400 aag aag ttt ttc ctc cag gag agc cct gtt ttc tat gtc cag aca tta     1248
Lys Lys Phe Phe Leu Gln Glu Ser Pro Val Phe Tyr Val Gln Thr Leu
                405                 410                 415 caa gac ccc agc aaa gct ctg gtc ttt gag gag gcc acc ttg tca tgg     1296
Gln Asp Pro Ser Lys Ala Leu Val Phe Glu Glu Ala Thr Leu Ser Trp
```

-continued

```
              420                 425                 430
caa cag acc tgt ccc ggg atc gtc aat ggg gca ctg gag ctg gag agg        1344
Gln Gln Thr Cys Pro Gly Ile Val Asn Gly Ala Leu Glu Leu Glu Arg
            435                 440                 445 aac ggg cat gct tct gag ggg atg acc agg cct aga gat gcc ctc ggg        1392
Asn Gly His Ala Ser Glu Gly Met Thr Arg Pro Arg Asp Ala Leu Gly
        450                 455                 460 cca gag gaa gaa ggg aac agc ctg ggc cca gag ttg cac aag atc aac        1440
Pro Glu Glu Glu Gly Asn Ser Leu Gly Pro Glu Leu His Lys Ile Asn
465                 470                 475                 480 ctg gtg gtg gct atg ctg tcc caa cac ttg tat gtc ctc ctt ggc ttg        1488
Leu Val Val Ala Met Leu Ser Gln His Leu Tyr Val Leu Leu Gly Leu
                485                 490                 495 cag ggg atg atg tta ggg gtc tgc ggc aac acg ggg agt ggt aag agc        1536
Gln Gly Met Met Leu Gly Val Cys Gly Asn Thr Gly Ser Gly Lys Ser
            500                 505                 510 agc ctg ttg tca gcc atc ctg gag gag atg cac ttg ctc gag ggc tcg        1584
Ser Leu Leu Ser Ala Ile Leu Glu Glu Met His Leu Leu Glu Gly Ser
        515                 520                 525 gtg ggg gtg cag gga agc ctg gcc tat gtc ccc cag cag gcc tgg atc        1632
Val Gly Val Gln Gly Ser Leu Ala Tyr Val Pro Gln Gln Ala Trp Ile
530                 535                 540 gtc agc ggg aac atc agg gag aac atc ctc atg gga ggc gca tat gac        1680
Val Ser Gly Asn Ile Arg Glu Asn Ile Leu Met Gly Gly Ala Tyr Asp
545                 550                 555                 560 aag gcc cga tac ctc cag gtg ctc cac tgc tgc tcc ctg aat cgg gac        1728
Lys Ala Arg Tyr Leu Gln Val Leu His Cys Cys Ser Leu Asn Arg Asp
                565                 570                 575 ctg gaa ctt ctg ccc ttt gga gac atg aca gag att gga gag cgg ggc        1776
Leu Glu Leu Leu Pro Phe Gly Asp Met Thr Glu Ile Gly Glu Arg Gly
            580                 585                 590 ctc aac ctc tct ggg ggg cag aaa cag agg atc agc ctg gcc cgc gcc        1824
Leu Asn Leu Ser Gly Gly Gln Lys Gln Arg Ile Ser Leu Ala Arg Ala
        595                 600                 605 gtc tat tcc gac cgt cag atc tac ctg ctg gac gac ccc ctg tct gct        1872
Val Tyr Ser Asp Arg Gln Ile Tyr Leu Leu Asp Asp Pro Leu Ser Ala
610                 615                 620 gtg gac gcc cac gtg ggg aag cac att ttt gag gag tgc att aag aag        1920
Val Asp Ala His Val Gly Lys His Ile Phe Glu Glu Cys Ile Lys Lys
625                 630                 635                 640 aca ctc agg ggg aag acg gtc gtc ctg gtg acc cac cag ctg cag tac        1968
Thr Leu Arg Gly Lys Thr Val Val Leu Val Thr His Gln Leu Gln Tyr
                645                 650                 655 tta gaa ttt tgt ggc cag atc att ttg ttg gaa aat ggg aaa atc tgt        2016
Leu Glu Phe Cys Gly Gln Ile Ile Leu Leu Glu Asn Gly Lys Ile Cys
            660                 665                 670 gaa aat gga act cac agt gag tta atg cag aaa aag ggg aaa tat gcc        2064
Glu Asn Gly Thr His Ser Glu Leu Met Gln Lys Lys Gly Lys Tyr Ala
        675                 680                 685 caa ctt atc cag aag atg cac aag gaa gcc act tcg gtg agt cct gcc        2112
Gln Leu Ile Gln Lys Met His Lys Glu Ala Thr Ser Val Ser Pro Ala
690                 695                 700 cca ctg ccc tca cta ccc acg gtg gac gca cgt gta ctc agg gcc tgt        2160
Pro Leu Pro Ser Leu Pro Thr Val Asp Ala Arg Val Leu Arg Ala Cys
705                 710                 715                 720 gct ctc tcc cca gga cat gtt gca gga cac agc aaa gat agc aga gaa        2208
Ala Leu Ser Pro Gly His Val Ala Gly His Ser Lys Asp Ser Arg Glu
                725                 730                 735 gcc aaa gtg ccg gag cat cag ctc aca cag gag gag gag atg gaa gaa        2256
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Ala | Lys | Val | Pro | Glu | His | Gln | Leu | Thr | Gln | Glu | Glu | Met | Glu | Glu |      |
|     |     |     | 740 |     |     |     | 745 |     |     |     | 750 |     |     |     |      |
| ggc | tcc | ttg | agt | tgg | agg | gtc | tac | cac | cac | tac | atc | cag | gca | gct | gga  | 2304 |
| Gly | Ser | Leu | Ser | Trp | Arg | Val | Tyr | His | His | Tyr | Ile | Gln | Ala | Ala | Gly  |
|     | 755 |     |     |     |     | 760 |     |     |     |     | 765 |     |     |     |      |
| ggt | tac | atg | gtc | tct | tgc | ata | att | ttc | ttc | ttc | gtg | gtg | ctg | atc | gtc  | 2352 |
| Gly | Tyr | Met | Val | Ser | Cys | Ile | Ile | Phe | Phe | Phe | Val | Val | Leu | Ile | Val  |
|     | 770 |     |     |     | 775 |     |     |     |     | 780 |     |     |     |     |      |
| ttc | tta | acg | atc | ttc | agc | ttc | tgg | tgg | ctg | agc | tac | tgg | ttg | gag | cag  | 2400 |
| Phe | Leu | Thr | Ile | Phe | Ser | Phe | Trp | Trp | Leu | Ser | Tyr | Trp | Leu | Glu | Gln  |
| 785 |     |     |     |     | 790 |     |     |     |     | 795 |     |     |     |     | 800  |
| ggc | tcg | ggg | gtg | agt | gcc | atg | agc | cga | gag | agc | aat | gga | acc | atg | gca  | 2448 |
| Gly | Ser | Gly | Val | Ser | Ala | Met | Ser | Arg | Glu | Ser | Asn | Gly | Thr | Met | Ala  |
|     |     |     |     | 805 |     |     |     |     | 810 |     |     |     |     | 815 |      |
| gac | ctg | ggc | aac | att | gca | gac | aat | cct | caa | ctg | tcc | ttc | tac | cag | ctg  | 2496 |
| Asp | Leu | Gly | Asn | Ile | Ala | Asp | Asn | Pro | Gln | Leu | Ser | Phe | Tyr | Gln | Leu  |
|     |     |     | 820 |     |     |     |     | 825 |     |     |     |     | 830 |     |      |
| gtg | tac | ggg | ctc | aac | gcc | ctg | ctc | ctc | atc | tgt | gtg | ggg | gtc | tgc | tcc  | 2544 |
| Val | Tyr | Gly | Leu | Asn | Ala | Leu | Leu | Leu | Ile | Cys | Val | Gly | Val | Cys | Ser  |
|     |     | 835 |     |     |     |     | 840 |     |     |     |     | 845 |     |     |      |
| tca | ggg | att | ttc | acc | aaa | gtc | acg | agg | aag | gca | tcc | acg | gcc | ctg | cac  | 2592 |
| Ser | Gly | Ile | Phe | Thr | Lys | Val | Thr | Arg | Lys | Ala | Ser | Thr | Ala | Leu | His  |
|     | 850 |     |     |     |     | 855 |     |     |     |     | 860 |     |     |     |      |
| aac | aag | ctc | ttc | aac | aag | gtt | ttc | cgc | tgc | ccc | atg | agt | ttc | ttt | gac  | 2640 |
| Asn | Lys | Leu | Phe | Asn | Lys | Val | Phe | Arg | Cys | Pro | Met | Ser | Phe | Phe | Asp  |
| 865 |     |     |     |     | 870 |     |     |     |     | 875 |     |     |     |     | 880  |
| acc | atc | cca | ata | ggc | cgg | ctt | ttg | aac | tgc | ttc | gca | ggg | gac | ttg | gaa  | 2688 |
| Thr | Ile | Pro | Ile | Gly | Arg | Leu | Leu | Asn | Cys | Phe | Ala | Gly | Asp | Leu | Glu  |
|     |     |     |     | 885 |     |     |     |     | 890 |     |     |     |     | 895 |      |
| cag | ctg | gac | cag | ctc | ttg | ccc | atc | ttt | tca | gag | cag | ttc | ctg | gtc | ctg  | 2736 |
| Gln | Leu | Asp | Gln | Leu | Leu | Pro | Ile | Phe | Ser | Glu | Gln | Phe | Leu | Val | Leu  |
|     |     |     | 900 |     |     |     |     | 905 |     |     |     |     | 910 |     |      |
| tcc | tta | atg | gtg | atc | gcc | gtc | ctg | ttg | att | gtc | agt | gtg | ctg | tct | cca  | 2784 |
| Ser | Leu | Met | Val | Ile | Ala | Val | Leu | Leu | Ile | Val | Ser | Val | Leu | Ser | Pro  |
|     |     | 915 |     |     |     |     | 920 |     |     |     |     | 925 |     |     |      |
| tat | atc | ctg | tta | atg | gga | gcc | ata | atc | atg | gtt | att | tgc | ttc | att | tat  | 2832 |
| Tyr | Ile | Leu | Leu | Met | Gly | Ala | Ile | Ile | Met | Val | Ile | Cys | Phe | Ile | Tyr  |
|     | 930 |     |     |     |     | 935 |     |     |     |     | 940 |     |     |     |      |
| tat | atg | atg | ttc | aag | aag | gcc | atc | ggt | gtg | ttc | aag | aga | ctg | gag | aac  | 2880 |
| Tyr | Met | Met | Phe | Lys | Lys | Ala | Ile | Gly | Val | Phe | Lys | Arg | Leu | Glu | Asn  |
| 945 |     |     |     |     | 950 |     |     |     |     | 955 |     |     |     |     | 960  |
| tat | agc | cgg | tct | cct | tta | ttc | tcc | cac | atc | ctc | aat | tct | ctg | caa | ggc  | 2928 |
| Tyr | Ser | Arg | Ser | Pro | Leu | Phe | Ser | His | Ile | Leu | Asn | Ser | Leu | Gln | Gly  |
|     |     |     |     | 965 |     |     |     |     | 970 |     |     |     |     | 975 |      |
| ctg | agc | tcc | atc | cat | gtc | tat | gga | aaa | act | gaa | gac | ttc | atc | agc | cag  | 2976 |
| Leu | Ser | Ser | Ile | His | Val | Tyr | Gly | Lys | Thr | Glu | Asp | Phe | Ile | Ser | Gln  |
|     |     |     | 980 |     |     |     |     | 985 |     |     |     |     | 990 |     |      |
| ttt | aag | agg | ctg | act | gat | gcg | cag | aat | aac | tac | ctg | ctg | ttg | ttt | cta  | 3024 |
| Phe | Lys | Arg | Leu | Thr | Asp | Ala | Gln | Asn | Asn | Tyr | Leu | Leu | Leu | Phe | Leu  |
|     |     | 995 |     |     |     |     | 1000|     |     |     |     | 1005|     |     |      |
| tct | tcc | aca | cga | tgg | atg | gca | ttg | agg | ctg | gag | atc | atg | acc | aac |      | 3069 |
| Ser | Ser | Thr | Arg | Trp | Met | Ala | Leu | Arg | Leu | Glu | Ile | Met | Thr | Asn |      |
|     |     | 1010|     |     |     | 1015|     |     |     |     | 1020|     |     |     |      |
| ctt | gtg | acc | ttg | gct | gtt | gcc | ctg | ttc | gtg | gct | ttt | ggc | att | tcc |      | 3114 |
| Leu | Val | Thr | Leu | Ala | Val | Ala | Leu | Phe | Val | Ala | Phe | Gly | Ile | Ser |      |
|     |     | 1025|     |     |     | 1030|     |     |     |     | 1035|     |     |     |      |
| tcc | acc | ccc | tac | tcc | ttt | aaa | gtc | atg | gct | gtc | aac | atc | gtg | ctg |      | 3159 |
| Ser | Thr | Pro | Tyr | Ser | Phe | Lys | Val | Met | Ala | Val | Asn | Ile | Val | Leu |      |
|     |     | 1040|     |     |     | 1045|     |     |     |     | 1050|     |     |     |      |

-continued

| | | |
|---|---|---|
| cag ctg gcg tcc agc ttc cag gcc act gcc cgg att ggc ttg gag<br>Gln Leu Ala Ser Ser Phe Gln Ala Thr Ala Arg Ile Gly Leu Glu<br>1055                             1060                              1065 | | 3204 |
| aca gag gca cag ttc acg gct gta gag agg ata ctg cag tac atg<br>Thr Glu Ala Gln Phe Thr Ala Val Glu Arg Ile Leu Gln Tyr Met<br>1070                             1075                             1080 | | 3249 |
| aag atg tgt gtc tcg gaa gct cct tta cac atg gaa ggc aca agt<br>Lys Met Cys Val Ser Glu Ala Pro Leu His Met Glu Gly Thr Ser<br>1085                             1090                             1095 | | 3294 |
| tgt ccc cag ggg tgg cca cag cat ggg gaa atc ata ttt cag gat<br>Cys Pro Gln Gly Trp Pro Gln His Gly Glu Ile Ile Phe Gln Asp<br>1100                             1105                             1110 | | 3339 |
| tat cac atg aaa tac aga gac aac aca ccc acc gtg ctt cac ggc<br>Tyr His Met Lys Tyr Arg Asp Asn Thr Pro Thr Val Leu His Gly<br>1115                             1120                             1125 | | 3384 |
| atc aac ctg acc atc cgc ggc cac gaa gtg gtg ggc atc gtg gga<br>Ile Asn Leu Thr Ile Arg Gly His Glu Val Val Gly Ile Val Gly<br>1130                             1135                             1140 | | 3429 |
| agg acg ggc tct ggg aag tcc tcc ttg ggc atg gct ctc ttc cgc<br>Arg Thr Gly Ser Gly Lys Ser Ser Leu Gly Met Ala Leu Phe Arg<br>1145                             1150                             1155 | | 3474 |
| ctg gtg gag ccc atg gca ggc cgg att ctc att gac ggc gtg gac<br>Leu Val Glu Pro Met Ala Gly Arg Ile Leu Ile Asp Gly Val Asp<br>1160                             1165                             1170 | | 3519 |
| att tgc agc atc ggc ctg gag gac ttg cgg tcc aag ctc tca gtg<br>Ile Cys Ser Ile Gly Leu Glu Asp Leu Arg Ser Lys Leu Ser Val<br>1175                             1180                             1185 | | 3564 |
| atc cct caa gat cca gtg ctg ctc tca gga acc atc aga ttc aac<br>Ile Pro Gln Asp Pro Val Leu Leu Ser Gly Thr Ile Arg Phe Asn<br>1190                             1195                             1200 | | 3609 |
| cta gat ccc ttt gac cgt cac act gac cag cag atc tgg gat gcc<br>Leu Asp Pro Phe Asp Arg His Thr Asp Gln Gln Ile Trp Asp Ala<br>1205                             1210                             1215 | | 3654 |
| ttg gag agg aca ttc ctg acc aag gcc atc tca aag ttc ccc aaa<br>Leu Glu Arg Thr Phe Leu Thr Lys Ala Ile Ser Lys Phe Pro Lys<br>1220                             1225                             1230 | | 3699 |
| aag ctg cat aca gat gtg gtg gaa aac ggt gga aac ttc tct gtg<br>Lys Leu His Thr Asp Val Val Glu Asn Gly Gly Asn Phe Ser Val<br>1235                             1240                             1245 | | 3744 |
| ggg gag agg cag ctg ctc tgc att gcc agg gct gtg ctt cgc aac<br>Gly Glu Arg Gln Leu Leu Cys Ile Ala Arg Ala Val Leu Arg Asn<br>1250                             1255                             1260 | | 3789 |
| tcc aag atc atc ctt atc gat gaa gcc aca gcc tcc att gac atg<br>Ser Lys Ile Ile Leu Ile Asp Glu Ala Thr Ala Ser Ile Asp Met<br>1265                             1270                             1275 | | 3834 |
| gag aca gac acc ctg atc cag cgc aca atc cgt gaa gcc ttc cag<br>Glu Thr Asp Thr Leu Ile Gln Arg Thr Ile Arg Glu Ala Phe Gln<br>1280                             1285                             1290 | | 3879 |
| ggc tgc acc gtg ctc gtc att gcc cac cgt gtc acc act gtg ctg<br>Gly Cys Thr Val Leu Val Ile Ala His Arg Val Thr Thr Val Leu<br>1295                             1300                             1305 | | 3924 |
| aac tgt gac cac atc ctg gtt atg ggc aat ggg aag gtg gta gaa<br>Asn Cys Asp His Ile Leu Val Met Gly Asn Gly Lys Val Val Glu<br>1310                             1315                             1320 | | 3969 |
| ttt gat cgg ccg gag gta ctg cgg aag aag cct ggg tca ttg ttc<br>Phe Asp Arg Pro Glu Val Leu Arg Lys Lys Pro Gly Ser Leu Phe<br>1325                             1330                             1335 | | 4014 |
| gca gcc ctc atg gcc aca gcc<br>Ala Ala Leu Met Ala Thr Ala<br>1340                             1345 | | 4035 |

<210> SEQ ID NO 2
<211> LENGTH: 1345
<212> TYPE: PRT
<213> ORGANISM: Homo sapiens

<400> SEQUENCE: 2

| | | | | | | | | | | | | | | | |
|---|---|---|---|---|---|---|---|---|---|---|---|---|---|---|---|
| Met | Thr | Arg | Lys | Arg | Thr | Tyr | Trp | Val | Pro | Asn | Ser | Ser | Gly | Gly | Leu |
| 1 | | | | 5 | | | | | 10 | | | | | 15 | |
| Val | Asn | Arg | Gly | Ile | Asp | Ile | Gly | Asp | Asp | Met | Val | Ser | Gly | Leu | Ile |
| | | | 20 | | | | | 25 | | | | | 30 | | |
| Tyr | Pro | Leu | Asp | Asn | Ala | Gly | Leu | Phe | Ser | Tyr | Leu | Thr | Val | Ser | Trp |
| | | | 35 | | | | | 40 | | | | | 45 | | |
| Leu | Thr | Pro | Leu | Met | Ile | Gln | Ser | Leu | Arg | Ser | Arg | Leu | Asp | Glu | Asn |
| | 50 | | | | | 55 | | | | | 60 | | | | |
| Thr | Ile | Pro | Pro | Leu | Ser | Val | His | Asp | Ala | Ser | Asp | Lys | Asn | Val | Gln |
| 65 | | | | | 70 | | | | | 75 | | | | | 80 |
| Arg | Leu | His | Arg | Leu | Trp | Glu | Glu | Val | Ser | Arg | Arg | Gly | Ile | Glu | |
| | | | | 85 | | | | | 90 | | | | | 95 | |
| Lys | Ala | Ser | Val | Leu | Leu | Val | Met | Leu | Arg | Phe | Gln | Arg | Thr | Arg | Leu |
| | | | 100 | | | | | 105 | | | | | 110 | | |
| Ile | Phe | Asp | Ala | Leu | Leu | Gly | Ile | Cys | Phe | Cys | Ile | Ala | Ser | Val | Leu |
| | | | 115 | | | | | 120 | | | | | 125 | | |
| Gly | Pro | Ile | Leu | Ile | Ile | Pro | Lys | Ile | Leu | Glu | Tyr | Ser | Glu | Glu | Gln |
| | 130 | | | | | 135 | | | | | 140 | | | | |
| Leu | Gly | Asn | Val | Val | His | Gly | Val | Gly | Leu | Cys | Phe | Ala | Leu | Phe | Leu |
| 145 | | | | | 150 | | | | | 155 | | | | | 160 |
| Ser | Glu | Cys | Val | Lys | Ser | Leu | Ser | Phe | Ser | Ser | Ser | Trp | Ile | Ile | Asn |
| | | | | 165 | | | | | 170 | | | | | 175 | |
| Gln | Arg | Thr | Ala | Ile | Arg | Phe | Arg | Ala | Ala | Val | Ser | Ser | Phe | Ala | Phe |
| | | | 180 | | | | | 185 | | | | | 190 | | |
| Glu | Lys | Leu | Ile | Gln | Phe | Lys | Ser | Val | Ile | His | Ile | Thr | Ser | Gly | Glu |
| | | | 195 | | | | | 200 | | | | | 205 | | |
| Ala | Ile | Ser | Phe | Phe | Thr | Gly | Asp | Val | Asn | Tyr | Leu | Phe | Glu | Gly | Val |
| | 210 | | | | | 215 | | | | | 220 | | | | |
| Cys | Tyr | Gly | Pro | Leu | Val | Leu | Ile | Thr | Cys | Ala | Ser | Leu | Val | Ile | Cys |
| 225 | | | | | 230 | | | | | 235 | | | | | 240 |
| Ser | Ile | Ser | Ser | Tyr | Phe | Ile | Ile | Gly | Tyr | Thr | Ala | Phe | Ile | Ala | Ile |
| | | | | 245 | | | | | 250 | | | | | 255 | |
| Leu | Cys | Tyr | Leu | Leu | Val | Phe | Pro | Leu | Ala | Val | Phe | Met | Thr | Arg | Met |
| | | | 260 | | | | | 265 | | | | | 270 | | |
| Ala | Val | Lys | Ala | Gln | His | His | Thr | Ser | Glu | Val | Ser | Asp | Gln | Arg | Ile |
| | | | 275 | | | | | 280 | | | | | 285 | | |
| Arg | Val | Thr | Ser | Glu | Val | Leu | Thr | Cys | Ile | Lys | Leu | Ile | Lys | Met | Tyr |
| | 290 | | | | | 295 | | | | | 300 | | | | |
| Thr | Trp | Glu | Lys | Pro | Phe | Ala | Lys | Ile | Ile | Glu | Asp | Leu | Arg | Arg | Lys |
| 305 | | | | | 310 | | | | | 315 | | | | | 320 |
| Glu | Arg | Lys | Leu | Leu | Glu | Lys | Cys | Gly | Leu | Val | Gln | Ser | Leu | Thr | Ser |
| | | | | 325 | | | | | 330 | | | | | 335 | |
| Ile | Thr | Leu | Phe | Ile | Ile | Pro | Thr | Val | Ala | Thr | Ala | Val | Trp | Val | Leu |
| | | | 340 | | | | | 345 | | | | | 350 | | |
| Ile | His | Thr | Ser | Leu | Lys | Leu | Lys | Leu | Thr | Ala | Ser | Met | Ala | Phe | Ser |
| | | | 355 | | | | | 360 | | | | | 365 | | |
| Met | Leu | Ala | Ser | Leu | Asn | Leu | Leu | Arg | Leu | Ser | Val | Phe | Phe | Val | Pro |

-continued

```
            370                 375                 380
Ile Ala Val Lys Gly Leu Thr Asn Ser Lys Ser Ala Val Met Arg Phe
385                 390                 395                 400

Lys Lys Phe Phe Leu Gln Glu Ser Pro Val Phe Tyr Val Gln Thr Leu
                405                 410                 415

Gln Asp Pro Ser Lys Ala Leu Val Phe Glu Glu Ala Thr Leu Ser Trp
                420                 425                 430

Gln Gln Thr Cys Pro Gly Ile Val Asn Gly Ala Leu Glu Leu Glu Arg
                435                 440                 445

Asn Gly His Ala Ser Glu Gly Met Thr Arg Pro Arg Asp Ala Leu Gly
    450                 455                 460

Pro Glu Glu Gly Asn Ser Leu Gly Pro Glu Leu His Lys Ile Asn
465                 470                 475                 480

Leu Val Val Ala Met Leu Ser Gln His Leu Tyr Val Leu Leu Gly Leu
                485                 490                 495

Gln Gly Met Met Leu Gly Val Cys Gly Asn Thr Gly Ser Gly Lys Ser
                500                 505                 510

Ser Leu Leu Ser Ala Ile Leu Glu Glu Met His Leu Leu Glu Gly Ser
    515                 520                 525

Val Gly Val Gln Gly Ser Leu Ala Tyr Val Pro Gln Gln Ala Trp Ile
    530                 535                 540

Val Ser Gly Asn Ile Arg Glu Asn Ile Leu Met Gly Gly Ala Tyr Asp
545                 550                 555                 560

Lys Ala Arg Tyr Leu Gln Val Leu His Cys Cys Ser Leu Asn Arg Asp
                565                 570                 575

Leu Glu Leu Leu Pro Phe Gly Asp Met Thr Glu Ile Gly Glu Arg Gly
                580                 585                 590

Leu Asn Leu Ser Gly Gly Gln Lys Gln Arg Ile Ser Leu Ala Arg Ala
    595                 600                 605

Val Tyr Ser Asp Arg Gln Ile Tyr Leu Leu Asp Asp Pro Leu Ser Ala
    610                 615                 620

Val Asp Ala His Val Gly Lys His Ile Phe Glu Glu Cys Ile Lys Lys
625                 630                 635                 640

Thr Leu Arg Gly Lys Thr Val Val Leu Val Thr His Gln Leu Gln Tyr
                645                 650                 655

Leu Glu Phe Cys Gly Gln Ile Ile Leu Leu Glu Asn Gly Lys Ile Cys
                660                 665                 670

Glu Asn Gly Thr His Ser Glu Leu Met Gln Lys Lys Gly Lys Tyr Ala
    675                 680                 685

Gln Leu Ile Gln Lys Met His Lys Glu Ala Thr Ser Val Ser Pro Ala
    690                 695                 700

Pro Leu Pro Ser Leu Pro Thr Val Asp Ala Arg Val Leu Arg Ala Cys
705                 710                 715                 720

Ala Leu Ser Pro Gly His Val Ala Gly His Ser Lys Asp Ser Arg Glu
                725                 730                 735

Ala Lys Val Pro Glu His Gln Leu Thr Gln Glu Glu Met Glu Glu
                740                 745                 750

Gly Ser Leu Ser Trp Arg Val Tyr His His Tyr Ile Gln Ala Ala Gly
    755                 760                 765

Gly Tyr Met Val Ser Cys Ile Ile Phe Phe Val Val Leu Ile Val
    770                 775                 780

Phe Leu Thr Ile Phe Ser Phe Trp Trp Leu Ser Tyr Trp Leu Glu Gln
785                 790                 795                 800
```

-continued

```
Gly Ser Gly Val Ser Ala Met Ser Arg Glu Ser Asn Gly Thr Met Ala
            805                 810                 815

Asp Leu Gly Asn Ile Ala Asp Asn Pro Gln Leu Ser Phe Tyr Gln Leu
            820                 825                 830

Val Tyr Gly Leu Asn Ala Leu Leu Ile Cys Val Gly Val Cys Ser
            835                 840                 845

Ser Gly Ile Phe Thr Lys Val Thr Arg Lys Ala Ser Thr Ala Leu His
    850                 855                 860

Asn Lys Leu Phe Asn Lys Val Phe Arg Cys Pro Met Ser Phe Phe Asp
865                 870                 875                 880

Thr Ile Pro Ile Gly Arg Leu Leu Asn Cys Phe Ala Gly Asp Leu Glu
                885                 890                 895

Gln Leu Asp Gln Leu Leu Pro Ile Phe Ser Glu Gln Phe Leu Val Leu
                900                 905                 910

Ser Leu Met Val Ile Ala Val Leu Leu Ile Val Ser Val Leu Ser Pro
                915                 920                 925

Tyr Ile Leu Leu Met Gly Ala Ile Ile Met Val Ile Cys Phe Ile Tyr
    930                 935                 940

Tyr Met Met Phe Lys Lys Ala Ile Gly Val Phe Lys Arg Leu Glu Asn
945                 950                 955                 960

Tyr Ser Arg Ser Pro Leu Phe Ser His Ile Leu Asn Ser Leu Gln Gly
                965                 970                 975

Leu Ser Ser Ile His Val Tyr Gly Lys Thr Glu Asp Phe Ile Ser Gln
                980                 985                 990

Phe Lys Arg Leu Thr Asp Ala Gln  Asn Asn Tyr Leu Leu  Leu Phe Leu
            995                 1000                1005

Ser Ser  Thr Arg Trp Met Ala  Leu Arg Leu Glu Ile  Met Thr Asn
    1010                1015                1020

Leu Val  Thr Leu Ala Val Ala  Leu Phe Val Ala Phe  Gly Ile Ser
    1025                1030                1035

Ser Thr  Pro Tyr Ser Phe Lys  Val Met Ala Val Asn  Ile Val Leu
    1040                1045                1050

Gln Leu  Ala Ser Ser Phe Gln  Ala Thr Ala Arg Ile  Gly Leu Glu
    1055                1060                1065

Thr Glu  Ala Gln Phe Thr Ala  Val Glu Arg Ile Leu  Gln Tyr Met
    1070                1075                1080

Lys Met  Cys Val Ser Glu Ala  Pro Leu His Met Glu  Gly Thr Ser
    1085                1090                1095

Cys Pro  Gln Gly Trp Pro Gln  His Gly Glu Ile Ile  Phe Gln Asp
    1100                1105                1110

Tyr His  Met Lys Tyr Arg Asp  Asn Thr Pro Thr Val  Leu His Gly
    1115                1120                1125

Ile Asn  Leu Thr Ile Arg Gly  His Glu Val Val Gly  Ile Val Gly
    1130                1135                1140

Arg Thr  Gly Ser Gly Lys Ser  Ser Leu Gly Met Ala  Leu Phe Arg
    1145                1150                1155

Leu Val  Glu Pro Met Ala Gly  Arg Ile Leu Ile Asp  Gly Val Asp
    1160                1165                1170

Ile Cys  Ser Ile Gly Leu Glu  Asp Leu Arg Ser Lys  Leu Ser Val
    1175                1180                1185

Ile Pro  Gln Asp Pro Val Leu  Leu Ser Gly Thr Ile  Arg Phe Asn
    1190                1195                1200
```

-continued

```
Leu Asp Pro Phe Asp Arg His Thr Asp Gln Gln Ile Trp Asp Ala
    1205                1210                1215

Leu Glu Arg Thr Phe Leu Thr Lys Ala Ile Ser Lys Phe Pro Lys
    1220                1225                1230

Lys Leu His Thr Asp Val Val Glu Asn Gly Gly Asn Phe Ser Val
    1235                1240                1245

Gly Glu Arg Gln Leu Leu Cys Ile Ala Arg Ala Val Leu Arg Asn
    1250                1255                1260

Ser Lys Ile Ile Leu Ile Asp Glu Ala Thr Ala Ser Ile Asp Met
    1265                1270                1275

Glu Thr Asp Thr Leu Ile Gln Arg Thr Ile Arg Glu Ala Phe Gln
    1280                1285                1290

Gly Cys Thr Val Leu Val Ile Ala His Arg Val Thr Thr Val Leu
    1295                1300                1305

Asn Cys Asp His Ile Leu Val Met Gly Asn Gly Lys Val Val Glu
    1310                1315                1320

Phe Asp Arg Pro Glu Val Leu Arg Lys Lys Pro Gly Ser Leu Phe
    1325                1330                1335

Ala Ala Leu Met Ala Thr Ala
    1340                1345

<210> SEQ ID NO 3
<211> LENGTH: 1345
<212> TYPE: PRT
<213> ORGANISM: Homo sapiens

<400> SEQUENCE: 3

Met Thr Arg Lys Arg Thr Tyr Trp Val Pro Asn Ser Ser Gly Gly Leu
1               5                   10                  15

Val Asn Arg Gly Ile Asp Ile Gly Asp Asp Met Val Ser Gly Leu Ile
                20                  25                  30

Tyr Pro Leu Asp Asn Ala Gly Leu Phe Ser Tyr Leu Thr Val Ser Trp
            35                  40                  45

Leu Thr Pro Leu Met Ile Gln Ser Leu Arg Ser Arg Leu Asp Glu Asn
    50                  55                  60

Thr Ile Pro Pro Leu Ser Val His Asp Ala Ser Asp Lys Asn Val Gln
65                  70                  75                  80

Arg Leu His Arg Leu Trp Glu Glu Val Ser Arg Arg Gly Ile Glu
                85                  90                  95

Lys Ala Ser Val Leu Leu Val Met Leu Arg Phe Gln Arg Thr Arg Leu
                100                 105                 110

Ile Phe Asp Ala Leu Leu Gly Ile Cys Phe Cys Ile Ala Ser Val Leu
            115                 120                 125

Gly Pro Ile Leu Ile Pro Lys Ile Leu Glu Tyr Ser Glu Glu Gln
    130                 135                 140

Leu Gly Asn Val Val His Gly Val Gly Leu Cys Phe Ala Leu Phe Leu
145                 150                 155                 160

Ser Glu Cys Val Lys Ser Leu Ser Phe Ser Ser Trp Ile Ile Asn
                165                 170                 175

Gln Arg Thr Ala Ile Arg Phe Arg Ala Ala Val Ser Ser Phe Ala Phe
            180                 185                 190

Glu Lys Leu Ile Gln Phe Lys Ser Val Ile His Ile Thr Ser Gly Glu
        195                 200                 205

Ala Ile Ser Phe Phe Thr Gly Asp Val Asn Tyr Leu Phe Glu Gly Val
    210                 215                 220
```

-continued

```
Cys Tyr Gly Pro Leu Val Leu Ile Thr Cys Ala Ser Leu Val Ile Cys
225                 230                 235                 240

Ser Ile Ser Ser Tyr Phe Ile Ile Gly Tyr Thr Ala Phe Ile Ala Ile
            245                 250                 255

Leu Cys Tyr Leu Leu Val Phe Pro Leu Ala Val Phe Met Thr Arg Met
                260                 265                 270

Ala Val Lys Ala Gln His His Thr Ser Glu Val Ser Asp Gln Arg Ile
            275                 280                 285

Arg Val Thr Ser Glu Val Leu Thr Cys Ile Lys Leu Ile Lys Met Tyr
        290                 295                 300

Thr Trp Glu Lys Pro Phe Ala Lys Ile Ile Glu Asp Leu Arg Arg Lys
305                 310                 315                 320

Glu Arg Lys Leu Leu Glu Lys Cys Gly Leu Val Gln Ser Leu Thr Ser
                325                 330                 335

Ile Thr Leu Phe Ile Ile Pro Thr Val Ala Thr Ala Val Trp Val Leu
                340                 345                 350

Ile His Thr Ser Leu Lys Leu Lys Leu Thr Ala Ser Met Ala Phe Ser
        355                 360                 365

Met Leu Ala Ser Leu Asn Leu Leu Arg Leu Ser Val Phe Phe Val Pro
    370                 375                 380

Ile Ala Val Lys Gly Leu Thr Asn Ser Lys Ser Ala Val Met Arg Phe
385                 390                 395                 400

Lys Lys Phe Phe Leu Gln Glu Ser Pro Val Phe Tyr Val Gln Thr Leu
                405                 410                 415

Gln Asp Pro Ser Lys Ala Leu Val Phe Glu Glu Ala Thr Leu Ser Trp
            420                 425                 430

Gln Gln Thr Cys Pro Gly Ile Val Asn Gly Ala Leu Glu Leu Glu Arg
        435                 440                 445

Asn Gly His Ala Ser Glu Gly Met Thr Arg Pro Arg Asp Ala Leu Gly
    450                 455                 460

Pro Glu Glu Glu Gly Asn Ser Leu Gly Pro Glu Leu His Lys Ile Asn
465                 470                 475                 480

Leu Val Val Ala Met Leu Ser Gln His Leu Tyr Val Leu Leu Gly Leu
                485                 490                 495

Gln Gly Met Met Leu Gly Val Cys Gly Asn Thr Gly Ser Gly Lys Ser
            500                 505                 510

Ser Leu Leu Ser Ala Ile Leu Glu Glu Met His Leu Leu Glu Gly Ser
        515                 520                 525

Val Gly Val Gln Gly Ser Leu Ala Tyr Val Pro Gln Gln Ala Trp Ile
    530                 535                 540

Val Ser Gly Asn Ile Arg Glu Asn Ile Leu Met Gly Gly Ala Tyr Asp
545                 550                 555                 560

Lys Ala Arg Tyr Leu Gln Val Leu His Cys Cys Ser Leu Asn Arg Asp
                565                 570                 575

Leu Glu Leu Leu Pro Phe Gly Asp Met Thr Glu Ile Gly Glu Arg Gly
            580                 585                 590

Leu Asn Leu Ser Gly Gly Gln Lys Gln Arg Ile Ser Leu Ala Arg Ala
        595                 600                 605

Val Tyr Ser Asp Arg Gln Ile Tyr Leu Leu Asp Asp Pro Leu Ser Ala
    610                 615                 620

Val Asp Ala His Val Gly Lys His Ile Phe Glu Glu Cys Ile Lys Lys
625                 630                 635                 640
```

```
Thr Leu Arg Gly Lys Thr Val Leu Val Thr His Gln Leu Gln Tyr
            645             650             655

Leu Glu Phe Cys Gly Gln Ile Ile Leu Leu Glu Asn Gly Lys Ile Cys
                660             665             670

Glu Asn Gly Thr His Ser Glu Leu Met Gln Lys Gly Lys Tyr Ala
            675             680             685

Gln Leu Ile Gln Lys Met His Lys Glu Ala Thr Ser Val Ser Pro Ala
    690              695             700

Pro Leu Pro Ser Leu Pro Thr Val Asp Ala Arg Val Leu Arg Ala Cys
705             710              715             720

Ala Leu Ser Pro Gly His Val Ala Gly Ser Lys Asp Ser Arg Glu
                725             730              735

Ala Lys Val Pro Glu His Gln Leu Thr Gln Glu Glu Met Glu Glu
            740             745             750

Gly Ser Leu Ser Trp Arg Val Tyr His His Tyr Ile Gln Ala Ala Gly
            755             760             765

Gly Tyr Met Val Ser Cys Ile Ile Phe Phe Val Val Leu Ile Val
    770             775             780

Phe Leu Thr Ile Phe Ser Phe Trp Trp Leu Ser Tyr Trp Leu Glu Gln
785             790             795             800

Gly Ser Gly Val Ser Ala Met Ser Arg Glu Ser Asn Gly Thr Met Ala
            805             810             815

Asp Leu Gly Asn Ile Ala Asp Asn Pro Gln Leu Ser Phe Tyr Gln Leu
            820             825             830

Val Tyr Gly Leu Asn Ala Leu Leu Leu Ile Cys Val Gly Val Cys Ser
    835             840             845

Ser Gly Ile Phe Thr Lys Val Thr Arg Lys Ala Ser Thr Ala Leu His
    850             855             860

Asn Lys Leu Phe Asn Lys Val Phe Arg Cys Pro Met Ser Phe Phe Asp
865             870             875             880

Thr Ile Pro Ile Gly Arg Leu Leu Asn Cys Phe Ala Gly Asp Leu Glu
            885             890             895

Gln Leu Asp Gln Leu Leu Pro Ile Phe Ser Glu Gln Phe Leu Val Leu
    900             905             910

Ser Leu Met Val Ile Ala Val Leu Leu Ile Val Ser Val Leu Ser Pro
    915             920             925

Tyr Ile Leu Leu Met Gly Ala Ile Ile Met Val Ile Cys Phe Ile Tyr
    930             935             940

Tyr Met Met Phe Lys Lys Ala Ile Gly Val Phe Lys Arg Leu Glu Asn
945             950             955             960

Tyr Ser Arg Ser Pro Leu Phe Ser His Ile Leu Asn Ser Leu Gln Gly
            965             970             975

Leu Ser Ser Ile His Val Tyr Gly Lys Thr Glu Asp Phe Ile Ser Gln
            980             985             990

Phe Lys Arg Leu Thr Asp Ala Gln Asn Asn Tyr Leu Leu Leu Phe Leu
    995              1000            1005

Ser Ser Thr Arg Trp Met Ala Leu Arg Leu Glu Ile Met Thr Asn
    1010            1015            1020

Leu Val Thr Leu Ala Val Ala Leu Phe Val Ala Phe Gly Ile Ser
    1025            1030            1035

Ser Thr Pro Tyr Ser Phe Lys Val Met Ala Val Asn Ile Val Leu
    1040            1045            1050

Gln Leu Ala Ser Ser Phe Gln Ala Thr Ala Arg Ile Gly Leu Glu
```

-continued

```
            1055                1060                1065

Thr Glu Ala Gln Phe Thr Ala Val Glu Arg Ile Leu Gln Tyr Met
        1070                1075                1080

Lys Met Cys Val Ser Glu Ala Pro Leu His Met Glu Gly Thr Ser
        1085                1090                1095

Cys Pro Gln Gly Trp Pro Gln His Gly Glu Ile Ile Phe Gln Asp
        1100                1105                1110

Tyr His Met Lys Tyr Arg Asp Asn Thr Pro Thr Val Leu His Gly
        1115                1120                1125

Ile Asn Leu Thr Ile Arg Gly His Glu Val Val Gly Ile Val Gly
        1130                1135                1140

Arg Thr Gly Ser Gly Lys Ser Ser Leu Gly Met Ala Leu Phe Arg
        1145                1150                1155

Leu Val Glu Pro Met Ala Gly Arg Ile Leu Ile Asp Gly Val Asp
        1160                1165                1170

Ile Cys Ser Ile Gly Leu Glu Asp Leu Arg Ser Lys Leu Ser Val
        1175                1180                1185

Ile Pro Gln Asp Pro Val Leu Leu Ser Gly Thr Ile Arg Phe Asn
        1190                1195                1200

Leu Asp Pro Phe Asp Arg His Thr Asp Gln Gln Ile Trp Asp Ala
        1205                1210                1215

Leu Glu Arg Thr Phe Leu Thr Lys Ala Ile Ser Lys Phe Pro Lys
        1220                1225                1230

Lys Leu His Thr Asp Val Val Glu Asn Gly Gly Asn Phe Ser Val
        1235                1240                1245

Gly Glu Arg Gln Leu Leu Cys Ile Ala Arg Ala Val Leu Arg Asn
        1250                1255                1260

Ser Lys Ile Ile Leu Ile Asp Glu Ala Thr Ala Ser Ile Asp Met
        1265                1270                1275

Glu Thr Asp Thr Leu Ile Gln Arg Thr Ile Arg Glu Ala Phe Gln
        1280                1285                1290

Gly Cys Thr Val Leu Val Ile Ala His Arg Val Thr Thr Val Leu
        1295                1300                1305

Asn Cys Asp His Ile Leu Val Met Gly Asn Gly Lys Val Val Glu
        1310                1315                1320

Phe Asp Arg Pro Glu Val Leu Arg Lys Lys Pro Gly Ser Leu Phe
        1325                1330                1335

Ala Ala Leu Met Ala Thr Ala
        1340                1345

<210> SEQ ID NO 4
<211> LENGTH: 1436
<212> TYPE: PRT
<213> ORGANISM: Homo sapiens

<400> SEQUENCE: 4

Met Lys Asp Ile Asp Met Gly Lys Glu Tyr Ile Ile Pro Ser Pro Gly
1               5                   10                  15

Tyr Arg Ser Val Arg Asp Arg Ser Thr Ile Pro Gly Gln His Gly Asp
                20                  25                  30

Arg Glu Glu Pro Arg Phe Arg Arg Thr Arg Ser Leu Glu Cys Gln Asp
            35                  40                  45

Ala Leu Glu Thr Ala Ala Arg Val Glu Gly Leu Ser Leu Asp Ile Ser
        50                  55                  60
```

-continued

| | | | | | | | | | | | | | | |
|---|---|---|---|---|---|---|---|---|---|---|---|---|---|---|
| Val | His | Ser | His | Leu | Gln | Ile | Leu | Asp | Glu | Glu | His | Thr | Lys | Gly | Lys |
| 65 | | | | 70 | | | | 75 | | | | 80 | | | |

Tyr His His Gly Leu Ser Ala Leu Lys Pro Phe Arg Thr Thr Thr Lys
               85                       90                   95

His Gln His Pro Val Asp Asn Ala Gly Leu Phe Ser Tyr Met Thr Phe
           100                   105                   110

Ser Trp Leu Ser Pro Leu Ala Gln Val Val His Lys Lys Gly Glu Leu
       115                   120                  125

Leu Met Glu Asp Val Trp Pro Leu Ser Lys Tyr Glu Ser Ser Asp Val
130               135                  140

Asn Cys Arg Arg Leu Glu Arg Leu Trp Gln Glu Leu Asn Glu Val
145              150              155              160

Gly Pro Asp Ala Ala Ser Leu Arg Arg Val Val Trp Ile Phe Cys Arg
           165                   170                  175

Thr Arg Leu Ile Leu Ser Ile Val Cys Leu Met Ile Thr Gln Leu Ala
           180                   185                  190

Gly Phe Ser Gly Pro Ala Phe Val Val Lys His Leu Leu Glu Tyr Thr
           195                   200                  205

Gln Ala Thr Glu Ser Asn Leu Gln Tyr Ser Leu Leu Val Leu Gly
       210                   215                  220

Leu Leu Leu Thr Glu Val Val Arg Ser Trp Ser Leu Ala Leu Thr Trp
225              230              235              240

Ala Leu Asn Tyr Arg Thr Gly Val Arg Leu Arg Gly Ala Val Leu Thr
           245                   250                  255

Met Ala Phe Lys Lys Ile Leu Lys Leu Lys Asn Ile Lys Glu Lys Ser
           260                   265                  270

Leu Gly Glu Leu Ile Asn Ile Cys Ser Asn Asp Gly Gln Arg Met Phe
           275                   280                  285

Glu Ala Ala Ala Val Gly Ser Leu Leu Ala Gly Gly Pro Val Val Ala
       290                   295                  300

Ile Leu Gly Met Ile Tyr Asn Val Ile Ile Leu Gly Pro Thr Gly Phe
305              310              315              320

Leu Gly Ser Ala Val Phe Ile Leu Phe Tyr Pro Ala Met Met Phe Val
           325                   330                  335

Ser Arg Leu Thr Ala Tyr Phe Arg Arg Lys Cys Val Ala Ala Thr Asp
           340                   345                  350

Asp Arg Val Gln Lys Met Asn Glu Val Leu Thr Tyr Ile Lys Phe Ile
           355                   360                  365

Lys Met Tyr Ala Trp Val Lys Ala Phe Ser Gln Cys Val Gln Lys Ile
           370                   375                  380

Arg Glu Glu Glu Arg Ile Leu Glu Lys Ala Gly Tyr Phe Gln Ser
385              390              395              400

Ile Thr Val Gly Val Ala Pro Ile Val Val Ile Ala Ser Val Val
           405                   410                  415

Thr Phe Ser Val His Met Thr Leu Gly Phe Asp Leu Thr Ala Ala Gln
           420                   425                  430

Ala Phe Thr Val Val Thr Val Phe Asn Ser Met Thr Phe Ala Leu Lys
           435                   440                  445

Val Thr Pro Phe Ser Val Lys Ser Leu Ser Glu Ala Ser Val Ala Val
       450                   455                  460

Asp Arg Phe Lys Ser Leu Phe Leu Met Glu Glu Val His Met Ile Lys
465              470              475              480

Asn Lys Pro Ala Ser Pro His Ile Lys Ile Glu Met Lys Asn Ala Thr

-continued

```
                485                 490                 495
Leu Ala Trp Asp Ser Ser His Ser Ser Thr Gln Ser Ser Pro Lys Leu
            500                 505                 510

Thr Pro Lys Val Lys Lys Asp Lys Arg Ala Pro Lys Gly Lys Lys Glu
            515                 520                 525

Lys Ser Arg Gln Leu Gln His Thr Glu His Gln Ala Val Leu Ala Glu
            530                 535                 540

Gln Lys Gly His Leu Leu Asp Ser Asp Glu Arg Pro Ser Pro Glu
545                 550                 555                 560

Glu Glu Glu Gly Lys Gln Ile His Ala Gly Ser Met Arg Leu Gln Arg
                565                 570                 575

Thr Leu Tyr Asn Ile Asp Leu Glu Ile Glu Glu Gly Lys Leu Val Gly
            580                 585                 590

Ile Cys Gly Ser Val Gly Ser Gly Lys Thr Ser Leu Ile Ser Ala Ile
            595                 600                 605

Leu Gly Gln Met Thr Leu Leu Glu Gly Ser Ile Ala Val Ser Gly Thr
            610                 615                 620

Phe Ala Tyr Val Ala Gln Gln Ala Trp Ile Leu Asn Ala Thr Leu Arg
625                 630                 635                 640

Asp Asn Ile Leu Phe Gly Lys Glu Phe Asp Glu Glu Arg Tyr Asn Ser
                645                 650                 655

Val Leu Asn Ser Cys Cys Leu Arg Pro Asp Leu Ala Ile Leu Pro Asn
            660                 665                 670

Ser Asp Leu Thr Glu Ile Gly Glu Arg Gly Ala Asn Leu Ser Gly Gly
            675                 680                 685

Gln Arg Gln Arg Ile Ser Leu Ala Arg Ala Leu Tyr Ser Asp Arg Ser
690                 695                 700

Ile Tyr Ile Leu Asp Asp Pro Leu Ser Ala Leu Asp Ala His Val Gly
705                 710                 715                 720

Asn His Ile Phe Asn Ser Ala Ile Arg Lys Arg Leu Lys Ser Lys Thr
                725                 730                 735

Val Leu Phe Val Thr His Gln Leu Gln Tyr Leu Val Asp Cys Asp Glu
            740                 745                 750

Val Ile Phe Met Lys Glu Gly Cys Ile Thr Glu Arg Gly Thr His Glu
            755                 760                 765

Glu Leu Met Asn Leu Asn Gly Asp Tyr Ala Thr Ile Phe Asn Asn Leu
            770                 775                 780

Leu Leu Gly Glu Thr Pro Pro Val Glu Ile Asn Ser Lys Lys Glu Ala
785                 790                 795                 800

Ser Gly Ser Gln Lys Ser Gln Asp Lys Gly Pro Lys Pro Gly Ser Val
                805                 810                 815

Lys Lys Glu Lys Ala Val Lys Ser Glu Glu Gly Gln Leu Val Gln Val
            820                 825                 830

Glu Glu Lys Gly Gln Gly Ser Val Pro Trp Ser Val Tyr Trp Val Tyr
            835                 840                 845

Ile Gln Ala Ala Gly Gly Pro Leu Ala Phe Leu Val Ile Met Val Leu
            850                 855                 860

Phe Met Leu Asn Val Gly Ser Thr Ala Phe Ser Thr Trp Trp Leu Ser
865                 870                 875                 880

Tyr Trp Ile Lys Gln Gly Ser Gly Asn Ser Thr Val Phe Glu Gly Asn
                885                 890                 895

Arg Ser Ser Val Ser Asp Ser Met Arg Asp Asn Pro Phe Leu Gln Tyr
            900                 905                 910
```

```
Tyr Ala Ser Ile Tyr Ala Leu Ser Met Ala Val Met Leu Ile Leu Lys
        915                 920                 925

Ala Ile Arg Gly Val Val Phe Val Lys Gly Thr Leu Arg Ala Ser Ser
        930                 935                 940

Arg Leu His Asp Glu Leu Phe Arg Arg Ile Leu Arg Ser Pro Met Lys
945                 950                 955                 960

Phe Phe Asp Thr Thr Pro Thr Gly Arg Ile Leu Asn Arg Phe Ser Lys
                965                 970                 975

Asp Met Asp Glu Val Asp Val Arg Leu Pro Phe Gln Ala Glu Met Phe
            980                 985                 990

Ile Gln Asn Val Ile Leu Val Phe Phe Cys Val Gly Met Ile Ala Gly
        995                 1000                1005

Val Phe Pro Trp Phe Leu Val Ala Val Gly Pro Leu Leu Ile Leu
    1010                1015                1020

Phe Ser Val Leu His Ile Val Ser Arg Val Leu Ile Arg Glu Leu
    1025                1030                1035

Lys Arg Leu Asp Asn Ile Thr Gln Ser Pro Phe Leu Ser His Ile
    1040                1045                1050

Thr Ser Ser Ile Gln Gly Leu Ala Thr Ile His Ala Tyr Asn Lys
    1055                1060                1065

Arg Gln Glu Phe Leu His Arg Tyr Gln Glu Leu Leu Asp Asp Asn
    1070                1075                1080

Gln Ala Pro Phe Phe Leu Phe Thr Cys Ala Met Arg Trp Leu Ala
    1085                1090                1095

Val Arg Leu Asp Leu Ile Ser Ile Ala Leu Ile Thr Thr Thr Gly
    1100                1105                1110

Leu Met Ile Val Leu Met His Gly Gln Ile Pro Ser Ala Tyr Ala
    1115                1120                1125

Gly Leu Ala Ile Ser Tyr Ala Val Gln Leu Thr Gly Leu Phe Gln
    1130                1135                1140

Phe Thr Val Arg Leu Ala Ser Glu Thr Glu Ala Arg Phe Thr Ser
    1145                1150                1155

Val Glu Arg Ile Asn His Tyr Ile Lys Thr Leu Ser Leu Glu Ala
    1160                1165                1170

Pro Ala Arg Ile Lys Asn Lys Ala Pro Pro His Asp Trp Pro Gln
    1175                1180                1185

Glu Gly Glu Ile Thr Phe Glu Asn Ala Glu Met Arg Tyr Arg Glu
    1190                1195                1200

Asn Leu Pro Leu Val Leu Lys Lys Val Ser Phe Thr Ile Lys Pro
    1205                1210                1215

Lys Glu Lys Ile Gly Ile Val Gly Arg Thr Gly Ser Gly Lys Ser
    1220                1225                1230

Ser Leu Gly Met Ala Leu Phe Arg Leu Val Glu Leu Ser Gly Gly
    1235                1240                1245

Cys Ile Lys Ile Asp Gly Val Arg Ile Ser Asp Ile Gly Leu Ala
    1250                1255                1260

Asp Leu Arg Ser Lys Leu Thr Ile Ile Pro Gln Glu Pro Val Leu
    1265                1270                1275

Phe Ser Gly Thr Val Arg Ser Asn Leu Asp Pro Phe Asn Gln Tyr
    1280                1285                1290

Thr Glu Glu Gln Ile Trp Asp Ala Leu Glu Arg Thr His Met Lys
    1295                1300                1305
```

| Glu | Cys | Ile | Ala | Gln | Leu | Pro | Leu | Lys | Leu | Glu | Ser | Glu | Val | Met |
|     | 1310|     |     |     | 1315|     |     |     |     | 1320|     |     |     |     |

| Glu | Asn | Gly | Asp | Asn | Phe | Ser | Val | Gly | Glu | Arg | Gln | Leu | Leu | Cys |
|     | 1325|     |     |     |     | 1330|     |     |     |     | 1335|     |     |     |

| Ile | Ala | Arg | Ala | Leu | Leu | Arg | His | Cys | Lys | Ile | Leu | Ile | Leu | Asp |
|     | 1340|     |     |     |     | 1345|     |     |     |     | 1350|     |     |     |

| Glu | Ala | Thr | Ala | Ala | Met | Asp | Thr | Glu | Thr | Asp | Leu | Leu | Ile | Gln |
|     | 1355|     |     |     |     | 1360|     |     |     |     | 1365|     |     |     |

| Glu | Thr | Ile | Arg | Glu | Ala | Phe | Ala | Asp | Cys | Thr | Met | Leu | Thr | Ile |
|     | 1370|     |     |     |     | 1375|     |     |     |     | 1380|     |     |     |

| Ala | His | Arg | Leu | His | Thr | Val | Leu | Gly | Ser | Asp | Arg | Ile | Met | Val |
|     | 1385|     |     |     |     | 1390|     |     |     |     | 1395|     |     |     |

| Leu | Ala | Gln | Gly | Gln | Val | Val | Glu | Phe | Asp | Thr | Pro | Ser | Val | Leu |
|     | 1400|     |     |     |     | 1405|     |     |     |     | 1410|     |     |     |

| Leu | Ser | Asn | Asp | Ser | Ser | Arg | Phe | Tyr | Ala | Met | Cys | Ala | Ala | Ala |
|     | 1415|     |     |     |     | 1420|     |     |     |     | 1425|     |     |     |

| Glu | Asn | Lys | Val | Ala | Val | Lys | Gly |
|     | 1430|     |     |     |     | 1435|     |

<210> SEQ ID NO 5
<211> LENGTH: 398
<212> TYPE: DNA
<213> ORGANISM: Homo sapiens

<400> SEQUENCE: 5

```
ggtggatcat caaccaacgc gacagccatc aggttccgag cagctgtttc ctcctttgcc      60
tttgagaagc tcatccaatt taagtctgta atacacatca cctcaggaga ggccatcagc     120
ttcttcaccg gtgatgtaaa ctacctgttt gaagggtgt gctatggacc cctagtactg     180
atcacctgcg catcgctggt catctgcagc atttcttcct acttcattat ggatacact     240
gcatttattg ccatcttatg ctatctcctg gttttcccat ggcggtatt catgacaaga     300
atggctgtga aggctcggca tcacacatct gaggtcagcg accagcgcat ccgtgtgacc     360
agtgaagttc tcacttgcat taagctgatt aaaatgta                             398
```

<210> SEQ ID NO 6
<211> LENGTH: 290
<212> TYPE: DNA
<213> ORGANISM: Homo sapiens

<400> SEQUENCE: 6

```
tgtggtctgg actcgctggt ggctggtagg gcacattaaa gtcccttta cctaggagag      60
cccccaaggt cctggagggc agtggggccc tgggcactgt gcctgctgag ccaggcaggc    120
tctgtccctt ggcccaattg gtcctgaggc tggactcatt ctgccgcaga tgcacttgct    180
cgagggctcg gtgggggtgc agggaagcct ggcctatgtc ccccagcagg cctggatcgt    240
cagcgggaac atcagggaga acatcctcat gggaggcgca tatgacaagg               290
```

<210> SEQ ID NO 7
<211> LENGTH: 888
<212> TYPE: DNA
<213> ORGANISM: Homo sapiens
<220> FEATURE:
<221> NAME/KEY: misc_feature
<222> LOCATION: (731)..(731)
<223> OTHER INFORMATION: n = a, t, g, or c

<400> SEQUENCE: 7

```
atgacagccc aggatggtgc tttgcagcga tgtgcccttc agaaggcggc tccgcaccag    60
ctgcaggttg cgggccgagt ccacgctggt gcgcatggtg gagccgggca gcaggacgcc   120
ctcgtgggtg agcagcacgc gggaggcgac tggggatctg gatggggctc actgatgaca   180
tgctggcagc ctttcgcact gggggctgtc aaaaagagcc agacagacag ctgccccgg    240 cctgccccgc agtcaccaaa cctcagaccc gcctccacgc ctccgcttcc ggctacgcgc   300
tacggtccgt ccccgggccc aaaagccatg gcttcgcgct gctctctagg agagcctccc   360
gaattggcag gaactgaaaa tgactaggaa gaggacatac tgggtgccca actcttctgg   420
tggcctcgtg aatcgtggca tcgacatagg cgatgacatg gtttcaggac ttatttataa   480
aacctatact ctccaaagat ggcccctgga gtcagcaaga gagacatcct gaggctccag   540
ggagggcagc tgtcccaccg tggcggaagt aatgatgcct gccttgagaa ccatgattcc   600
ctttccgtcc aagccgaggt ttcctgcca cccaggccct ggacaagtgg ttgggcatgt    660
tcttcgtaac ctcaccgtgt catggtcacc ccgtcatgaa tccaaagctt acaggagtcg   720
gttagatgga ngcaaccatc cctccactgt cagggcaggg attggcctcg gaccagaatt   780
gtcagcggtt acacggcttt gagaaaaaga cgctaaggcg gggctgacac agccagccgc   840
cacggtgagc agatacacag tgtgggtctc gaagcgaggc aggacgtg              888
```

<210> SEQ ID NO 8
<211> LENGTH: 17
<212> TYPE: DNA
<213> ORGANISM: Homo sapiens
<220> FEATURE:
<221> NAME/KEY: misc_feature
<223> OTHER INFORMATION: MRP5-like protein forward primer
<400> SEQUENCE: 8
gcagctggcg tccagct                                                  17

<210> SEQ ID NO 9
<211> LENGTH: 22
<212> TYPE: DNA
<213> ORGANISM: Homo sapiens
<220> FEATURE:
<221> NAME/KEY: misc_feature
<223> OTHER INFORMATION: MRP5-like protein reverse primer
<400> SEQUENCE: 9
tgcagtatcc tctctacagc cg                                            22

<210> SEQ ID NO 10
<211> LENGTH: 21
<212> TYPE: DNA
<213> ORGANISM: Homo sapiens
<220> FEATURE:
<221> NAME/KEY: misc_feature
<223> OTHER INFORMATION: fluorogenic probe
<400> SEQUENCE: 10
cactgcccgg attggcttgg a                                             21